(12) United States Patent
Mulligan-Kehoe et al.

(10) Patent No.: US 7,241,446 B2
(45) Date of Patent: Jul. 10, 2007

(54) METHODS FOR MODULATING ANGIOGENESIS VIA VEGF

(75) Inventors: Mary Jo Mulligan-Kehoe, Enfield, NH (US); Richard J. Powell, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 36 days.

(21) Appl. No.: 10/506,225

(22) PCT Filed: Apr. 1, 2003

(86) PCT No.: PCT/US03/09981

§ 371 (c)(1),
(2), (4) Date: Dec. 20, 2004

(87) PCT Pub. No.: WO03/084483

PCT Pub. Date: Oct. 16, 2003

(65) Prior Publication Data

US 2005/0215466 A1 Sep. 29, 2005

Related U.S. Application Data

(60) Provisional application No. 60/448,301, filed on Feb. 14, 2003, provisional application No. 60/369,392, filed on Apr. 1, 2002.

(51) Int. Cl.
*A61K 39/00* (2006.01)
*A61K 38/16* (2006.01)
*A61K 38/17* (2006.01)

(52) U.S. Cl. .................. 424/184.1; 424/185.1

(58) Field of Classification Search ............. 424/184.1, 424/185.1
See application file for complete search history.

(56) References Cited

U.S. PATENT DOCUMENTS 6,235,713 B1 5/2001 Achen et al.

OTHER PUBLICATIONS

Mullingan-Kehoe et al, J Biol Chem 276(11): 8588-8596, Mar. 2001.*
Mason et al, Molecular Endocrinology 8(3): 325-332, 1994.*
Gura et al, Science 278: 1041-1042, Nov. 1997.*
Dermer, Bio/Technology 12: 320, 1994.*
Kang et al., "Cloning and characterization of human ubiquitin-processing protease-43 from terminally differentiated human melanoma cells using a rapid subtraction hybridization protocol RaSH", Gene 2001 267:233-242.
Kitareewan et al., "UBE1L is a retinoid target that triggers PML/RARα degradation and apoptosis in acute promyelocytic leukemia", Proc. Natl. Acad. Sci. USA 2002 99: (6) :3806-3811.
Mulligan-Kehoe et al., "A Truncated Plasminogen Activator Inhibitor-1 Protein Blocks the Availability of Heparin-binding Vascular Endothelial Growth Factor A Isoforms", J Biol Chem 2002 277 (50) :49077-49089.

* cited by examiner

Primary Examiner—Christina Chan
Assistant Examiner—Phuong Huynh
(74) Attorney, Agent, or Firm—Licata & Tyrrell P.C.

(57) ABSTRACT

Recombinant plasminogen activator inhibitor-1 (PAI-1) isoforms which lack the reactive center loop and contain the complete heparin-binding domain or lack at least a portion of the heparin-binding domain are described. The rPAI-1 isoforms disclosed herein may be used to modulate angiogenesis through blocking release of VEGF from a VEGF-heparin complex. Furthermore the rPAI-1 proteins may be used to inhibit cell proliferation and migration, induce apoptosis, and produce proteolytic fragments corresponding to angiostatin kringles 1–3 and kringles 1–4.

1 Claim, 1 Drawing Sheet

HUMAN PAI-1

Figure 1:
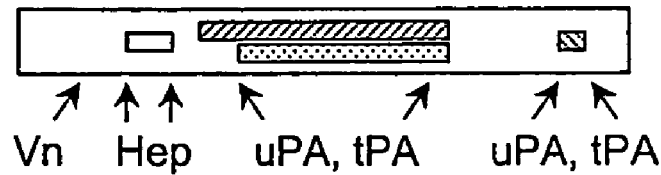
Figure 1:
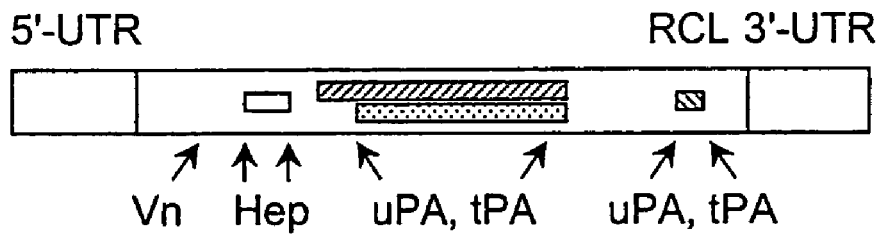
Figure 1:
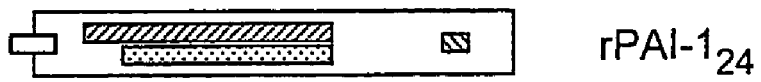
Figure 1:
Figure 1:
Figure 1:

| | | |
|---|---|---|
| □ HEPARIN 80-88 Lys-Lys | ▨ UROKINASE 110-145 FIBRIN 110 & 145 THROMBIN 115-148 VITRONECTIN (Vn) 110-145 | ▨ uPA 128-145 tPA 128-145 | ▨ uPA 346 tPA 346 |

PORCINE PAI-1 rPAI-1₂₄ rPAI-1₂₃ rPAI-1_Δ23 rPAI-1_Hep23

SEQUENCE LISTING

<160> NUMBER OF SEQ ID NOS: 8

<210> SEQ ID NO 1
<211> LENGTH: 27
<212> TYPE: PRT
<213> ORGANISM: Sus scrofa

<400> SEQUENCE: 1

Met Gln Phe Lys Ile Glu Glu Lys Gly Met Ala Pro Ala Leu Arg Gln
1               5                   10                  15

Leu Tyr Lys Glu Leu Met Gly Pro Trp Asn Lys
            20                  25

<210> SEQ ID NO 2
<211> LENGTH: 24
<212> TYPE: PRT
<213> ORGANISM: Sus scrofa

<400> SEQUENCE: 2

Lys Ile Glu Glu Lys Gly Met Ala Pro Ala Leu Arg Gln Leu Tyr Lys
1               5                   10                  15

Glu Leu Met Gly Pro Trp Asn Lys
            20

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide primer.

<400> SEQUENCE: 3
ggaattcatg gatgagatca gcacgg                                          26

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide primer.

<400> SEQUENCE: 4
gctctagatt tccactggct gatg                                            24

<210> SEQ ID NO 5
<211> LENGTH: 34
<212> TYPE: DNA
<213> ORGANISM: Artificial Sequence
<220> FEATURE:

-continued

```
<223> OTHER INFORMATION: Synthetic oligonucleotide primer.

<400> SEQUENCE: 5
ggaattcatg cagttcaaga ttgaggagaa gggc                              34

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide primer.

<400> SEQUENCE: 6
gctctagatt tccactggct gatg                                         24

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 7
ggaattcaag gagctcatgg                                              20

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 8
gctctagatc aaggctccat cac                                          23
```

METHODS FOR MODULATING ANGIOGENESIS VIA VEGF

ITRODUCTION

This application claims the benefit of U.S. Provisional Application No. 60/369,392 filed Apr. 1, 2002 and U.S. Provisional Application No. 60/448,301 filed Feb. 14, 2003.

This invention was supported in part by funds from the U.S. government (NIH NHLB1 Grant No. RO1-HL59590) and the U.S. government may therefore have certain rights in the invention.

BACKGROUND OF THE INVENTION

Angiogenesis is the formation of new capillary blood vessels as outgrowths of pre-existing vessels. The tightly regulated process plays a vital role in many physiological processes, such as embryogenesis, wound healing and menstruation. Angiogenesis is also important in certain pathological events. In addition to a role in solid tumor growth and metastasis, other notable conditions with an angiogenic component are arthritis, psoriasis and diabetic retinopathy (Hanahan and Folkman (1996) *Cell* 86:353–364; Fidler and Ellis (1994) *Cell* 79(2):185–188).

At the onset of angiogenesis, the quiescent endothelium is destabilized into migratory, proliferative endothelial cells. The angiogenic (activated) endothelium is maintained primarily by positive regulatory molecules. In the absence of such molecules, the endothelium remains in a differentiated, quiescent state that is maintained by negative regulatory molecules, angiogenesis inhibitors (Bouck (1990) *Cancer Cells* 2:179–185; Hanahan and Folkman (1996) supra). Normally, the negative and positive activities are balanced to maintain the vascular endothelium in quiescence (Hanahan and Folkman (1996) supra; Folkman and Klagsbrum (1987) *Science* 235:442–447). A shift in the balance of the positive and negative regulatory molecules can alter the differentiated state of the endothelium from the non-angiogenic, quiescent to the angiogenic state (Hanahan and Folkman (1996) supra). In the switch to pro-angiogenesis, the quiescent endothelial cells are stimulated to migrate toward a chemotactic stimulus, lining up in a tube (sprout) formation (Folkman and Klagsbrum (1987) supra). These cells also secrete proteolytic enzymes that degrade the endothelial basement membrane, thus allowing the migrating endothelial cells to extend into the perivascular stroma to begin a new capillary sprout. The angiogenic process is characterized by increased proliferation of endothelial cells to form the extending capillary (Folkman and Klagsbrum (1987) supra; Moses, et al. (1995) *Int. Rev. Cytol.* 161:1–48; Martiny-Baron and Marme (1995) *Curr. Opin. Biotechnol.* 6:675–680; Liotta, et al. (1991) *Cell* 64:327–336).

Vascular endothelial growth factor (VEGF) is a mitogenic factor that stimulates pro-angiogenic properties, including endothelial cell migration and proliferation. VEGF induces the expression of plasminogen activator proteolytic pathway proteins that participate in cellular invasive and remodeling processes (Pepper, et al. (1991) *Biochem. Biophys. Res. Commun.* 181:902–906; Mandriota, et al. (1995) *J. Biol. Chem.* 270:9709–9716; Mignatti, et al. (1989) *J. Cell. Biol.* 108:671–682). VEGF-A RNA can undergo alternative splicing to produce four isoforms (Leung, et al. (1989) *Science* 246:1306–1309; Houck, et al. (1991) *Mol. Endocriniology* 5:1806–1814; Tischer, et al. (1991) *J. Biol. Chem.* 26611947-22954). Three of those isoforms, VEGF-$A_{165,189,206}$, bind to heparin. Pro-VEGF affinity for heparin appears to be important in the regulation of the availability of VEGF at the cell surface (Houck, et al. (1992) *J. Biol. Chem.* 267:26031–26037), where it can interact with its tyrosine kinase receptors to exert its activity (Gitay-Goren, et al. (1992) *J. Biol. Chem.* 267:6093–6098). VEGF-A can be released from heparin in an inactive or active form (Ortega, et al. (1998) *Biol. Cell* 90:381–390). Plasmin and urokinase plasminogen activator (uPA) cleaves pro-VEGF into an active form of varied sizes depending upon the isoform and the activator molecule (Plouet, et al. (1997) *J. Biol. Chem.* 272:13390–13396).

There are naturally occurring molecules that serve as negative regulators of angiogenesis. Angiostatin, one such negative regulator, is a 38–45 kDa cleavage product of plasminogen, containing kringle domains 1–4 (K1–4) (O'Reilly, et al. (1994) *Cell* 79:315–328; O'Reilly, et al. (1996) *Nat. Med.* 2:689–692). Plasminogen, the precursor of plasmin, is activated when it is cleaved at the carboxy-terminus by plasminogen activators. The amino terminus contains five consecutive kringle domains, each approximately 9 kDa. The greatest inhibitory activity of angiostatin is contained within kringles 1–3 (Cao, et al. (1996) *J. Biol. Chem.* 271:29461–29467) and kringles 1–5 (Cao (1999) *Proc. Natl. Acad. Sci. USA* 6:5728–5733). The mechanism for angiostatin inhibition of endothelial cell growth in vitro and angiogenesis in vivo is unclear.

Plasminogen activator inhibitor-1 (PAI-1), a serpin family, serine protease inhibitor, is a multifunctional regulatory protein in the plasminogen activator proteolytic (Chapman, et al. (1982) *Cell* 28:653–662; Chapman (1997) *Curr. Opin. Cell Biol.* 9:714–724) and fibrinolytic pathways (Loskutoff and Curriden (1990) *Ann. NY Acad. Sci.* 598:238–247; Collen (1999) *Thromb. Haemost.* 82:258–270). Active PAI-1 (vitronectin-bound) inhibits proteolytic degradation of the extracellular matrix by inhibiting uPA/tPA, which in turn inhibits cell migration and invasion (Blasi (1999) *Thromb. Haemost.* 82:298–304). PAI-1 can exist in an active, inactive/latent or substrate-cleaved conformation (Lawrence, et al. (1997) *J. Biol. Chem.* 272:7676–7680; Debrock and Declerck (1998) *Thromb. Haemost.* 79:597–601). The PAI-1 reactive center loop (RCL), located at amino acids 320–351 (Schechter and Berger (1967) *Biochem. Biophys. Res. Commun.* 27:157–162; Laskowski and Kato (1980) *Annu. Rev. Biochem.* 49:593–626), initially interacts with uPA at Arg-346 (Lawrence, et al. (1994) *J. Biol. Chem.* 269:27657–27662; Tucker and Gerard (1996) *Eur. J. Biochem.* 237:180–187) to form a stable PAI-1/uPA complex to inactivate uPA (York, et al. (1991) *J. Biol. Chem.* 266:8495–8500). In the active/latent configuration of PAI-1 (not bound to vitronectin), the RCL spontaneously inserts into the β-sheet of strand 4a to stabilize the PAI-1 structure (Mottonen, et al. (1992) *Nature* 355:270–273; Egelund, et al. (1997) *Eur. J. Biochem.* 248:775–785; Kjoller, et al. (1996) *Eur. J. Biochem.* 241:38–46). It has been shown that when PAI-1 is cleaved between residues P and P' in the RCL, PAI-1 is converted to a substrate (Lawrence, et al. (1997) supra; Debrock and Declerck (1998) supra). In the cleaved conformation, the RCL is partially inserted into β-sheet of strand A, thus making the structure of cleaved and inactive PAI-1 more similar to each other than to active PAI-1. However, it has been demonstrated that there are distinct conformational differences between latent and cleaved PAI-1 (Sancho (1995) *Biochemistry* 34:1064–1069). The PAI-1 region distant from the RCL contains many binding domains for regulatory molecules involved in the proteolytic and fibrinolytic pathways. This region of PAI-1 has interactive sites for vitronectin (Lawrence, et al. (1994) supra;

Padmanabhan and Sane (1995) *Thromb. Haemost.* 73:829–834; Van Meijer, et al. (1994) *FEBS Lett.* 352: 342–346; Seiffert, et al. (1994) *J. Biol. Chem.* 269:2659–2666), heparin (Ehrlich, et al. (1992) *J. Biol. Chem.* 267:11606–11611), tPA, uPA (Keijer, et al. (1991) *Blood* 78:401–409; Reilly and Hutzelmann (1992) *J. Biol. Chem.* 267:17128–17135), thrombin (Ehrlich, et al. (1992) supra), and fibrin (Ehrlich, et al. (1992) supra; Reilly and Hutzelmann (1992) supra). Through its interactions with some of the same regulatory molecules in the proteolytic and fibrinolytic pathways, it has been demonstrated that PAI-1 (active and inactive) is also able to play a role in antiangiogenic mechanisms (Mulligan-Kehoe, et al. (2001) *J. Biol. Chem.* 276:8588–8596; Schnaper, et al. (1995) *J. Cell Physiol.* 165:107–118; Stefansson, et al. (2001) *J. Biol. Chem.* 276:8135–8141).

A recent report demonstrates that when a truncated porcine PAI-1 protein rPAI-1$_{23}$, is incubated with plasminogen and uPA, it induces formation of an angiostatin-like protein that has proteolytic activity (Mulligan-Kehoe, et al. (2001) supra). In this reaction, angiostatin is formed from cleaved plasmin. uPA enhances the formation of the angiostatin-like protein by increasing the amount of available plasmin. The proteolytic activity of the 36 kDa angiostatin is ultimately inhibited by increasing amounts of rPAI-1$_{23}$ that are available for binding uPA and/or plasminogen. In this second mechanism, rPAI-1$_{23}$ reduces the numbers of uPA/plasminogen interactions; thus, reducing the amount of plasmin produced. Cultured endothelial cells exposed to rPAI-1$_{23}$ exhibit a decrease in proliferation, increased apoptosis, and decreased migration in the presence of VEGF. This truncated PAI-1 appears to be exposing sites that participate in a functional role for PAI-1 in generating angiostatin fragments from plasmin.

Previously, zymographic analysis demonstrated the importance of rPAI-1$_{23}$ interactions with uPA, plasminogen, and plasmin that result in angiostatin formation. Furthermore, it has been shown that rPAI-1$_{23}$ blocks migration of VEGF-stimulated endothelial cells (Mulligan-Kehoe, et al. (2001) supra).

Anti-angiogenic tumor treatment strategies are based upon inhibiting the proliferation of budding vessels, generally at the periphery of a solid tumor. These therapies are often applied to reduce the risk of micrometastasis or to inhibit further growth of a solid tumor after more conventional intervention (such as surgery or chemotherapy).

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (Siemeister et al. (1998) *Cancer Metastasis Rev.*, 17(2):241–248). Monoclonal antibodies against VEGF have been shown to inhibit human tumor xenograft growth and ascites formation in mice (Kim, et al. (1993) *Nature* 362: 841–844; Asano, et al. (1998) *Hybridoma* 17:185–90; Mesiano, et al. (1998) *Am. J. Pathol.* 153(4):1249–1256; Luo, et al. (1998) *Cancer Res.* 58(12):2594–2600; Borgstrom, et al. (1996) *Prostate* 35(1):1–10; Borgstrom, et al. (1998) *Anticancer Research* 19(5B):4203–11). Moreover, U.S. Pat. No. 6,342,221 to Thorpe, et al. discloses the use of anti-VEGF antibodies to specifically inhibit VEGF binding to the VEGFR-2 receptor.

Regulation of angiogenesis by PAI proteins has also been discussed. U.S. Pat. No. 5,830,880 to Sedlacek, et al. discloses the expression of PAI-1, PAI-2, PAI-3 and angiostatin through a gene therapy approach to inhibit angiogenesis. Furthermore, RCL mutants (residues 331–346) of PAI-1 have been disclosed in PCT Publication No. WO 97/39028 which are resistant to elastase inactivation and/or have a high affinity for vitronectin.

SUMMARY OF THE INVENTION

Angiogenesis is the process of blood vessel growth towards a tissue in need of oxygen or an injured tissue. Angiogenesis can be either harmful or beneficial, for example, in cases such as tumor growth, angiogenesis towards the tumor can supply the tumor with nutrients and support its growth, thus further harming the patient. However, in occlusive (clotting of blood vessels) diseases, the ability to spontaneously develop collateral vessels often determines the level of tissue viability. Thus, methods of stimulating or inhibiting angiogenic processes are needed; The present invention meets this need by providing recombinant PAI-1 proteins useful in stimulating or inhibiting angiogenesis.

One aspect of the present invention is a method of modulating angiogenesis with a PAI-1 isoform. The method involves administering an effective amount of a PAI-1 isoform lacking the RCL domain and containing a complete heparin-binding domain or lacking at least a portion of the heparin-binding domain so that angiogenesis is modulated. In one embodiment, the PAI-1 isoform lacking both the RCL domain and at least a portion of the heparin-binding domain is useful in blocking or decreasing angiogenesis. In a preferred embodiment, a PAI-1 isoform for blocking or decreasing angiogenesis includes rPAI-1$_{23}$ and rPAI-1$_{A23}$. In another embodiment, the PAI-1 isoform lacking the RCL domain and containing a complete heparin-binding domain is useful in stimulating or increasing angiogenesis. In a preferred embodiment, a PAI-1 isoform for increasing or stimulating angiogenesis includes rPAI-1$_{Hep23}$. In a further embodiment, the PAI-1 isoform lacking the RCL domain and at least a portion of the heparin-binding domain is useful to block the release of VEGF from a VEGF-heparin complex thereby blocking angiogenesis. In another preferred embodiment of the present invention, the PAI-1 isoform for blocking the release of VEGF includes rPAI-1$_{23}$.

Other aspects of the present invention include methods of stimulating apoptosis or reducing cell proliferation or migration. These methods involve administering an effective amount of a PAI-1 isofrom which lacks both the RCL and heparin-binding domains. In a preferred embodiment, a PAI-1 isoform for stimulating apoptosis or reducing cell proliferation or migration includes rPAI-1$_{A23}$.

Another aspect of the present invention is a method of modulating angiostatin formation. The method involves administering a PAI-1 isoform which lacks an RCL domain and lacks at least a portion of a heparin-binding domain so that angiostatin containing kringle 1–3 or kringle 1–4 is formed. In a preferred embodiment, a PAI-1 isoform for modulating angiostatin formation includes rPAI-1$_{23}$ and rPAI-1$_{A23}$.

A still further aspect of the present invention is a method of treating an angiogenesis-mediated disease. The method involves administering either a proangiogenic or anti-angiogenic isoform of PAI-1 so that the signs or symptoms of an angiogenesis-mediated disease are reduced. In one embodiment of the present invention, an anti-angiogenic PAI-1 isoform lacks an RCL domain and lacks at least a portion of a heparin-binding domain. In a preferred embodiment, the anti-angiogenic PAI-1 isoforms include rPAI-1$_{23}$ and rPAI-1$_{A23}$. In another embodiment, of the present invention, a proagiogenic PAI-1 isoform lacks an RCL domain and contains a complete heparin-binding domain. In a preferred embodiment, the proangiogenic PAI-1 isoform includes rPAI-1$_{Hep23}$.

BRIED DESCRIPTION OF THE DRAWINGS

FIG. 1 illustrates rPAI-1 truncations relative to the human and porcine proteins. The domains that interact with specific molecules in the proteolytic, fibrinolytic and adhesion processes are indicated with arrows and bars. Overlapping domains are indicated. Deletions were based on the alignment of the human and porcine genes.

DETAILED DESCRIPTION OF THE INVENTION

The present invention provides methods of modulating angiogenesis through recombinant PAI-1 (rPAI-1) protein interactions. Four isoforms of rPAI-1 were generated, with and without the heparin-binding domain and the reactive center loop (FIG. 1, Table 1), and used to dissect the function of PAI-1.

TABLE 1

| Isoform | Heparin-Binding Domain | RCL Domain |
| --- | --- | --- |
| rPAI-1$_{Hep23}$ | Not deleted | Deleted |
| rPAI-1$_{24}$ | Partial Deletion | Not Deleted |
| rPAI-1$_{A23}$ | Deleted | Deleted |
| rPAI-1$_{23}$ | Partial Deletion | Deleted |

There are no known functional differences between human (huPAI-1) and porcine PAI-1 (poPAI-1) (Bijnens, et al. ((1997) *Thromb. Haemost.* 77:350–356; Bosma, et al. (1988) *J. Biol. Chem.* 263:9129–9141). Two of the rPAI-1 proteins, rPAI-1$_{Hep23}$ and rPAI-1$_{A23}$ are encoded by DNA sequence identical to the rPAI-1$_{23}$ (Mulligan-Kehoe, et al. (2001) supra) except that rPAI-1$_{Hep23}$ contains the codons for the entire heparin-binding domain, which have been completely deleted in rPAI-1$_{A23}$, and 21 additional amino acid residues at the N-terminus (Met-Gln-Phe-Lys-Ile-Glu-Glu-Lys-Gly-Met-Ala-Pro-Ala-Leu-Arg-Gln-Leu-Tyr-Lys-Glu-Leu-Met-Gly-Pro-Trp-Asn-Lys; SEQ ID NO:1). The rPAI-1$_{24}$ was the only rPAI-1 isoform that contained the reactive center loop (RCL) on the carboxyl terminus (amino acids 320–351). Amino acid residues 262–379 in mature poPAI-1 were deleted from the carboxyl termini of rPAI-1$_{23}$, rPAI-1$_{Hep23}$, and rPAI-1$_{A23}$. The RCL was within the deleted region and, therefore, enabled examination of the importance of a uPA site at residues 128–145, in the absence of the primary uPA site at Arg-346. The heparin-binding domain corresponding to amino acid residues 65–88 (Lys-Ile-Glu-Glu-Lys-Gly-Met-Ala-Pro-Ala-Leu-Arg-Gln-Leu-Tyr-Lys-Glu-Leu-Met-Gly-Pro-Trp-Asn-Lys; SEQ ID NO:2) was completely deleted in the rPAI-1$_{A23}$ isoform. The heparin-binding domain of rPAI-1$_{23}$ lacked amino acid residues 65–82.

As will be described in greater detail, three experimental approaches were used to demonstrate the impact that the four rPAI-1 isoforms had on angiogenic processes. The first approach was to examine the rPAI-1 protein interactions with heparin, uPA and plasminogen. The second approach explored the in vitro angiogenic activity of the rPAI-1 proteins through apoptosis, cell proliferation and migration experiments. A third approach looked at the interactions of a VEGF-heparin complex with rPAI-1 proteins, uPA, and plasmin and the effect on VEGF activation in rPAI-1-treated cells.

Protease activity was measured in reconstitution reactions combining recombinant, truncated rPAI-1 molecules with uPA and plasminogen with and without heparin. Zymographic analysis indicated that three of the four truncated PAI-1 proteins in combination with uPA and plasminogen resulted in the production of proteolytic fragments that migrated at 34–38 kDa. The rPAI-1$_{23}$ protein induced formation of two 34–38 kDa proteolytic angiostatin fragments from plasmin. However, the rPAI-1$_{A23}$ and rPAI-1$_{24}$ proteins each had a single band that corresponded to one of the 34–38 kDa fragments visualized in the rPAI-1$_{23}$ products. In the case of rPAI-1$_{A23}$, a proteolytic band appeared at or near the size of the lower proteolytic fragment induced by rPAI-1$_{23}$ cleavage of plasmin. The rPAI-1$_{24}$ protein induced a proteolytic fragment at or near the molecular mass corresponding to the larger of the two plasmin cleavage products induced by rPAI-1$_{23}$. The rPAI-1$_{Hep23}$ did not produce a proteolytic fragment at 34–38 kDa. The rPAI-1$_{23}$ protein (partial heparin-binding domain) maintained its activity when bound to heparin. Similarly, the proteolytic activity associated with a reaction mix containing uPA, plasminogen, and rPAI-1$_{Hep23}$ (complete heparin domain) was not altered in the presence of heparin. The rPAI-1$_{A23}$ protein (lacking a heparin-binding domain) and the rPAI-1$_{24}$ protein (containing the RCL and a partial heparin domain) did not demonstrate proteolytic plasmin cleavage products when incubated with heparin. The proteolytic proteins near 80 kDa corresponded to plasmin. Proteolytic proteins near 50 kDa may represent a different plasmin cleavage product containing a greater number of plasminogen kringle domains. The function of the rPAI-1$_{Hep23}$ isoform (complete heparin domain) in a reaction with uPA and plasminogen as compared with rPAI-1$_{23}$ isoform (partial heparin-binding domain) showed that binding to heparin did not alter the inability of rPAI-1$_{Hep23}$ to mediate the formation of proteolytic fragments at a molecular mass near 34 kDa. These experiments showed that a full heparin-binding domain may block the ability of PAI-1 to induce proteolytic proteins corresponding to or near the molecular mass of antiostatin containing K1–3.

In vitro analyses of angiostatin production following rPAI-1 treatment zymography analysis of proteolytic angiostatin in culture medium of rPAI-1-treated endothelial cells was conducted. The zymography analysis of the culture medium from rPAI-1$_{23}$-treated bovine aortic endothelial cells (BAEC) did not show proteolytic angiostatin at any of the examined time points (6, 15, 24, 36, 48, and 72 hours). On the other hand, the medium from the rPAI-1$_{A23}$-treated cells contained a substantial amount of proteolytic activity near 34 kDa in all of the examined time points. Analysis of the extracellular matrix proteins showed that proteolytic angiostatin was produced after 72 hours of rPAI-1$_{23}$ or rPAI-1$_{A23}$ treatment. The molecular mass of the proteolytic fragment in rPAI-1$_{A23}$-treated cells corresponded to the molecular mass that has been shown to contain angiostatin kringles 1–3 (Mulligan-Kehoe, et al. (2001) supra; Mulligan-Kehoe, et al. (1991) supra). The results indicate that rPAI-1$_{A23}$ is more efficient than rPAI-1$_{23}$ in producing proteolytic angiostatin in BAEC.

To further demonstrate that the plasminogen (plasmin) cleavage products formed in reconstitution reactions containing rPAI-1 proteins, uPA and plasminogen contained kringle domains 1–3, nitrocellulose membranes of said cleavage products were probed with anti-kringle 1–3 (angiostatin) antibodies. Samples containing 3, 15 or 30 nM of rPAI-1$_{23}$ had fragments containing kringles 1–3 at a molecular mass corresponding to the size that was visualized by zymography. Additionally, there were fragments containing kringles 1–3 at a molecular mass near 45 kDa that correspond to the reported size of kringles 1–4, and 70–80 kDa that correspond to the size of plasmin. The reaction product of 15 nM of rPAI-1$_{A23}$, uPA and plasminogen contained angiostatin kringles 1–3 at 34–36 kDa. However, that fragment was absent when 3 or 30 nM of rPAI-1$_{A23}$ were part of the reaction with uPA and plasminogen. In the reactions containing either rPAI-1$_{24}$ or rPAI-1$_{Hep23}$, plasminogen kringles 1–3 were not present at 34–36 kDa. There were detectable fragments containing kringles 1–3 near 45 kDa in the reactions containing 3 nM of rPAI-1$_{24}$. These data showed that the reaction of uPA and plasminogen with all concentrations of rPAI-1$_{23}$ resulted in the formation of plasminogen kringles 1–3 (angiostatin) at 34–36 kDa, which is consistent with the molecular mass of the proteolytic fragments observed on the zymogram. Additionally, there is a greater amount of kringles 1–3 at 45 kDa which is representative of a less potent angiostatin.

Immunoblot analyses of angiostatin in culture medium of rPAI-1-treated endothelial cells was also conducted. The results of the immunoblot analysis of the culture medium protein isolated from rPAI-1 treated or untreated BAEC showed that, at all three time points (24, 36, and 48 hours) and in all three test samples (no treatment, rPAI-1$_{23}$-treated, and rPAI-1$_{A23}$-treated), there were predominant proteins containing angiostatin kringles 1–3 at a molecular weight between 34 and 50 kDa and a less predominant fragment at 28 kDa. The kringles 1–3 fragments near 50 kDa were less intense in the rPAI-1$_{A23}$ samples at 24 hours, but they became more intense at each later time point. The rPAI-1$_{A23}$ samples at 36 and 48 hours displayed a pronounced K1–3 fragment between 28 and 34 kDa. In the 36 and 48 hour rPAI-1$_{23}$-treated cells, there was an additional processed/cleaved kringles 1–3 fragment beneath the fragment observed between 34 and 50 kDa. The 36 and 48 hour untreated samples did not contain additional cleavage products. The data from these experiments demonstrate that in rPAI-1$_{A23}$-treated cells at 36 and 48 hours, the fragments containing kringles 1–3 have undergone additional processing to result in angiostatin of a lower molecular mass; a size of angiostatin with greater anti-angiogenic activity (O'Reilly, et al. (1994) supra; Lucas, et al. (2000) *Biochemistry* 39:508–515; Cao, et al. (1999) supra; and O'Reilly, et al. (1996) supra). The amount of angiostatin is clearly in greater abundance in rPAI-1$_{A23}$-treated cells.

The results provided herein indicated that rPAI-1$_{23}$ may preferentially cleave plasminogen into angiostatin while rPAI-1$_{A23}$ may cleave plasmin into angiostatin with associated proteolytic activity. Thus, further analysis of angiostatin produced in biochemical reactions containing rPAI-1 proteins was performed wherein angiostatin was produced in varied permutations with rPAI-1 and uPA. This analysis provided a more extensive examination of the plasminogen/plasmin cleavage products in reactions containing either rPAI-1$_{23}$ or rPAI-1$_{A23}$ and two-chain uPA (tcuPA). Immunoblots, containing the products of the biochemical reactions, probed for angiostatin kringles 1–3, kringle 4, and mini-plasminogen were examined. In these reactions, the rPAI-1 protein was first reacted with 0.25 IU of tcuPA before adding 1 IU of plasminogen. The rPAI-1$_{23}$ samples contained kringles 1–3 (K1–3) at 28–34 kDa, 45 kDa, 50 kDa, and near 70 kDa. The intensity of the 34 kDa fragment increased with increasing concentrations of rPAI-1$_{23}$. At the highest concentration of rPAI-1$_{23}$ (30 nM), the 45 kDa K1–3 fragment was reduced and there was also a decrease in the 70 kDa fragment. In reactions containing rPAI-1$_{A23}$, the 24–28 kDa K1–3 fragments were only present when rPAI-1$_{A23}$ was at 15 nM. There were changes in the intensity of the fragments containing K1–3 at 45 and 50 kDa, which also appeared to be shifting upward. The intensity of plasmin at 70 kDa was not reduced in samples where the K1–3 fragments were increased.

When the same reactions were probed for kringle 4 (K4), there was a scant amount of K4 near 50 kDa in the reactions containing higher concentrations of rPAI-1$_{23}$ (15 and 30 nM)) and rPAI-1$_{A23}$. The greatest intensity was in the reaction which contained 15 nM of rPAI-1$_{A23}$. In the rPAI-1$_{A23}$ samples, there were two fragments near 45–50 kDa. There was not any detectable plasmin or plasminogen at 70–80 kDa in the reactions containing rPAI-1$_{23}$, but they were detectable in the rPAI-1$_{A23}$ samples. A mini-plasminogen (MP) probe of the reaction mixtures did not detect any fragments below 70 kDa and MP was only visible at levels slightly above background near 70 kDa.

Reaction mixtures were then probed for K1–3, K4, and MP in a permutation where uPA, plasminogen, and either rPAI-1$_{23}$ or rPAI-1$_{A23}$ were added simultaneously. In the K1–3-probed reactions containing rPAI-1$_{23}$, the K1–3 fragments at 28–34 kDa were nearly undetectable, the 45 and 50 kDa fragments in the samples containing 3 and 15 nM of rPAI-1$_{23}$ were intense, and intense K1–3 protein at 70–80 kDa was present at all concentrations of rPAI-1$_{23}$ (3, 15, and 30 nM). The reactions rPAI-1$_{A23}$ showed a dramatic difference in K1–3 fragments as compared to the rPAI-1$_{23}$ samples. The rFAI-1$_{A23}$ samples all displayed a distinct 28–34 kDa fragment. A less intense doublet near 45 kDa was visualized in samples containing 3 and 15 nM of rPAI-1$_{A23}$. The 50 and 70–80 kDa fragments were absent at all three concentrations of rPAI-1$_{A23}$ (3, 15, and 30 nM).

A K4 probe of the same reaction permutation containing rPAI-1$_{23}$ revealed the presence of angiostatin fragments near 45 kDa at all three concentrations of rPAI-1$_{23}$; a slight angiostatin fragment at 50 kDa in reactions containing 3 and 15 nM of rPAI-1$_{23}$; and K4 was not detectable near 70–80 kDa when rPAI-1$_{23}$ was present at 15 and 30 nM. A mini-plasminogen probe of the reaction mixture showed a fragment at 34 kDa when rPAI-1$_{23}$ was present at 15 and 30 nM. The MP fragment was of a slightly smaller molecular mass than the K4 probed fragments. The sample reaction mixtures containing rPAI-1$_{A23}$ did not reveal any detectable K4 or mini-plasminogen in this permutation.

The immunoblots indicated that there were differences in angiostatin produced in reactions with rPAI-1$_{23}$ and rPAI-1$_{A23}$. The differences were not only due to structural differences in rPAI-1, but were, also in part, due to molecular interactions that seemingly occurred in response to exposed domains in rPAI-1$_{23}$ and rPAI-1$_{A23}$. The alteration in angiostatin fragments containing K1–3 indicated that at high concentrations of rPAI-1$_{A23}$, which exceeded a 1:1 molar ratio with uPA, plasminogen was cleaved into angiostatin fragments near 34 kDa. However, in the permutation where all three molecules were allowed to interact simultaneously, the cleavage product was angiostatin containing K1–4 near 45 kDa. When rPAI-1$_{23}$ was in excess, then the K1–3 fragments at 50 and 45 kDa diminished in intensity. These data show that a fragment containing kringles 1–4 was the preferred cleavage product in a reaction where uPA first reacted with rPAI-1$_{A23}$ before plasminogen was added. When rPAI-1$_{A23}$, uPA and plasminogen were simultaneously added to a reaction, two sets of angiostatin fragments containing K1–3 were produced. While it appeared that the 34 kDa fragment was more abundant, there may have been two cleavage products at the onset or the K1–4 product may have underwent additional cleavage/processing to 34 kDa as rPAI-1$_{A23}$ concentrations were was increased. The significant difference in these reactions, when compared to the permutation where uPA was first reacted with rPAI-1$_{A23}$ before adding plasminogen, was the complete loss of plasmin and/or plasminogen. These collective data indicate that both rPAI-1$_{23}$ and rPAI-1$_{A23}$ may bind uPA and/or plasminogen and the varied interactions alter the cleavage site in plasminogen and/or plasmin.

As the data indicated that rPAI-1$_{23}$ and rPAI-1$_{A23}$ may cleave plasminogen, additional biochemical reactions were performed to analyze interactions of rPAI-1 with plasminogen. Increasing concentrations of rPAI-1$_{23}$ and rPAI-1$_{A23}$ were each incubated with plasminogen (without uPA) and then immunoblots containing each reaction mixture were probed for mini-plasminogen. The probed immunoblots revealed a distinct plasminogen cleavage product near 50 kDa in all reactions containing the rPAI-1$_{23}$ protein (3, 15 and 30 nM). In the same reactions, a corresponding decrease in plasminogen at 80 kDa was seen as well, clearly demonstrating that plasminogen was cleaved into the smaller product. In contrast, the rPAI-1$_{A23}$ protein did not cleave plasminogen, even when increasing concentrations of the recombinant protein were added. Based on the mini-plasminogen antibody recognition, the 50 kDa cleavage product contained either multiple kringle domains to include K5 or a combination of kringle domains and the serine protease domain. The data demonstrates that the rPAI-1$_{23}$ recombinant protein cleaves plasminogen, while the rPAI-1$_{A23}$ protein does not.

To evaluate which cleavage products in reactions containing rPAI-1$_{23}$ resulted from plasminogen vs. plasmin, the cleavage products in a reaction containing rPAI-1$_{23}$ and plasminogen were examined. Additionally, the effect that uPA may potentially have on rPAI-1$_{23}$ cleavage of plasminogen was examined. These experiments showed distinct rPAI-1-cleaved plasminogen fragments containing K1–3 at 50 kDa, between 28–34 kDa, and predominantly at 45 kDa. These data demonstrate that the 28–34 kDa angiostatin was K1–3 cleaved from plasminogen. As increasing concentrations of uPA were added to the rPAI-1$_{23}$·plasminogen complex, the K1–3 at 28–34 kDa diminished and was eventually undetectable. This showed that uPA was able to compete rPAI-1$_{23}$ away from plasminogen in a uPA dose-dependent manner. A decrease in the amount of plasmin at 72 kDa was seen as compared to the plasmin formed in a uPA and plasminogen reaction. The results of these experiments indicated that rPAI-1$_{23}$ cleaved plasminogen into angiostatin K1–3, a more potent angiostatin fragment (Cao, et al. (1996) supra); uPA could reverse that cleavage by competing rPAI-1$_{23}$ away from plasminogen; and rPAI-1$_{A23}$ does not cleave plasminogen. These results further indicate that the rPAI-1$_{23}$ protein has both binding capabilities which have the potential to ultimately regulate plasmin formation.

Results provided herein demonstrated rPAI-1$_{A23}$ did not cleave plasminogen, however the effect that uPA may have on the formation of angiostatin was not investigated in reactions containing rPAI-1$_{A23}$ and plasminogen. Therefore, analysis of angiostatin in biochemical reactions containing rPAI-1$_{A23}$, uPA and plasminogen was performed. As K4 and MP were not identified in reactions where rPAI-1$_{A23}$, uPA, and plasminogen were added simultaneously to a reaction, concentrations of plasminogen were increased to 2 IU in the next series of experiments where uPA and rPAI-1$_{A23}$ concentrations were varied. Biochemical reactions, containing rPAI-1$_{A23}$, uPA and plasminogen, were performed to identify differences in angiostatin production that may occur as a result of the order in which the molecules were added to the reaction mixture.

Immunoblots of products of a reaction where all three reactants were added simultaneously, then incubated at 37° C. for two hours showed two distinct subsets of proteins containing K1–3. One subset had a molecular mass of approximately 45 kDa, the size reported for angiostatin K1–4 (O'Reilly, et al. (1994) supra, Cao, et al. (1996) supra). The other subset of protein fragments had a molecular mass between 28 and 36 kDa, the size reported for angiostatin K1–3 (O'Reilly, et al. (1994) supra, Cao, et al. (1996) supra). The most observable differences in the two subsets of fragments containing K1–3 were the following. 1) The intensity of the 28–36 kDa protein fragments was greater than the 45 kDa fragments. 2) The intensity of the fragments near 45 kDa decreased as the concentration of rPAI-1$_{A23}$ was increased; as the uPA concentration was increased, the intensity of the 45 kDa fragments increased, but not to the level observed when rPAI-1$_{A23}$ was at the lowest concentration (3 nM). 3) As the concentration of rPAI-1$_{A23}$ was increased, there was a shift in the molecular mass of both subsets of fragments containing K1–3; the shift was greater when uPA was at lower concentrations, which indicated that an increase in uPA stabilized the reaction and the site of plasminogen/plasmin cleavage. Alternatively, uPA may be in sufficient quantity to eliminate competition between rPAI-1$_{A23}$ and plasminogen for uPA binding sites. 4) There were differences in the amount of plasmin or plasminogen that remained uncleaved when rPAI-1$_{A23}$ was part of the reaction. In reactions where uPA was at the highest concentration (0.25 Units), plasmin and plasminogen were not detectable. When uPA was reduced by one-fourth, greater amounts of plasmin and plasminogen remained uncleaved. These observations indicated that uPA was bound to rPAI-1$_{A23}$ when the rPAI-1$_{A23}$ was in excess, such that uPA was unavailable to cleave plasminogen to form plasmin.

Further analysis of the interaction of tcuPA with rPAI-1$_{A23}$ was conducted to determine if this interaction stabilized the cleavage of plasmin or plasminogen into angiostatin. The results of immunoblots of biochemical reactions in which rPAI-1$_{A23}$ and uPA were first reacted before adding plasminogen showed stabilized angiostatin fragments in two distinct subsets of fragments: one subset near 50 kDa and the other subset at 34 kDa. The intensity of the fragment near 50 kDa decreased with increasing amounts of rPAI-1$_{A23}$. The plasmin remaining in the reaction mixtures was undetectable at the higher concentrations of rPAI-1$_{A23}$, independent of the uPA concentration. Differences between the results of these experiments and those provided above were that the molecular mass of the angiostatin fragments did not shift when rPAI-1$_{A23}$ and uPA were reacted first before adding plasminogen, which indicated that the interaction between uPA and rPAI-1$_{A23}$ stabilized the cleavage of plasmin.

Results provided herein indicate a competition between rPAI-1$_{A23}$ and plasminogen for binding uPA to result in a fraction of uncleaved plasmin or plasminogen. Thus, plasmin was made in a reaction containing uPA and plasminogen before adding rPAI-1$_{A23}$. In these reactions, the two subsets of angiostatin fragments were produced. The angiostatin fragments shifted slightly upward when the concentration of rPAI-1$_{A23}$ was increased. There was a diminution in both subsets of the angiostatin fragments when 30 nM of rPAI-1$_{A23}$ was in the reaction mix. The proteins corresponding to the molecular mass of plasmin were absent when low concentrations of uPA were combined with middle concentrations of rPAI-1$_{A23}$ (15 nM) and when both uPA and rPAI-1$_{A23}$ were at their highest concentrations (0.25 Units and 30 nM, respectively). There was a greater intensity in plasminogen when the reactions contained the highest concentration rPAI-1$_{A23}$ (30 nM) and the low and mid concentrations of uPA (0.025 and 0.05 Units). Those same reactions also contained less angiostatin at 45 and 28–36 kDa, which indicated that: uPA conversion of plasminogen into plasmin was not exhausted after 1 hour, and that rPAI-1$_{A23}$ was unable to cleave the residual plasminogen; increasing concentrations of rPAI-1$_{A23}$ were able to compete with plasminogen for binding to uPA to result in a reduction in plasmin levels; or rPAI-1$_{A23}$ can bind a uPA/plasminogen complex, alter the conformation of uPA or plasminogen to result in inefficient conversion of plasminogen into plasmin or a reduction in epitope binding by the antibody.

The reaction mixtures, containing rPAI-1$_{A23}$, uPA and plasminogen reacted in varied permutations, were also probed for plasminogen K4. K4 was present at 45 kDa in all reactions where uPA was first reacted with rPAI-1$_{A23}$ before adding plasminogen. The intensity of the fragments at 45 kDa decreased when the rPAI-1$_{A23}$ concentration was increased and uPA was at low and mid concentrations. At the highest concentration of uPA (0.25 Units), the intensity of the fragments containing K4 declined at all concentrations of rPAI-1$_{A23}$ (3, 15, and 30 nM). Additionally, when plasmin was first made (uPA+plasminogen) before adding rPAI-1$_{A23}$, K4 was detectable at the 45 kDa range when rPAI-1$_{A23}$ was at low and mid concentrations (3 and 15 nM), but was absent when rPAI-1$_{A23}$ was at the high concentration (30 nM). There was a slight shift in the angiostatin K1–4 fragment as the uPA concentration was increased. When all three reactants were simultaneously added to the reaction mixture and the resulting reaction products were probed for plasminogen K4, there was very little evidence of kringle 4. It was slightly detectable at 45 kDa when rPAI-1$_{A23}$ was at the lowest concentration, but was not detectable at 28–38 kDa. These data indicated that the binding domain for K4 was unavailable in most of the reaction mixtures.

None of the reactions containing rPAI-1$_{A23}$ showed K4 at the molecular mass corresponding to plasminogen or plasmin. The subset of angiostatin fragments at 28–36 kDa was not present when probed for K4 thus providing verification that the 28–36 kDa was K1–3 and not K1–4. There was no evidence of K1–4 in the reaction mixtures where uPA and plasminogen were first reacted before 30 nM of rPAI-1$_{A23}$ was added. In these same samples, K1–3 were diminished at 45 kDa and 28–34 kDa. These combined data indicate that there was a conformational change in plasminogen and/or plasmin in both permutations, which made the epitopes for K1–3 and K4 less available and unavailable, respectively.

Plasminogen fragments were undetectable on immunoblots, containing plasminogen, uPA and rPAI-1$_{A23}$ reaction mixtures in all permutations, which were probed for miniplasmin (K5+the serine protease domain).

Collectively these data demonstrate that in reactions with uPA and plasminogen, the rPAI-1$_{A23}$ protein is responsible for the cleavage of plasmin into angiostatin K1–3 at 28–36 kDa and angiostatin K1–4 at 45 kDa. Plasminogen remained in the reactions containing 30 nM of rPAI-1$_{A23}$; thus validating the results which showed that rPAI-1$_{A23}$ was unable to cleave plasminogen. Increasing concentrations of uPA along with increasing concentrations of rPAI-1$_{A23}$ appear to reduce uPA interactions with plasminogen, which was further evidenced by a decrease in plasmin cleavage products.

The order in which the reactants were added appeared to alter the cleavage site in plasmin or plasminogen. In the biochemical reactions, an rPAI-1$_{A23}$·uPA complex stabilized the cleavage of plasmin into angiostatin K1–3 and K1–4.

The collective data indicated that tcuPA binds rPAI-1$_{A23}$. Therefore, experiments were performed to examine the interactions of rPAI-1$_{23}$ and rPAI-1$_{A23}$ with scuPA and tcuPA. Single-chain uPA was able to undergo a small degree of autocleavage, which was visible in the control scuPA as a fraction of tcuPA near 34 kDa. The data showed that when either rPAI-1$_{23}$ or rPAI-1$_{A23}$ were reacted with scuPA, there was a decrease in the amount of detectable scuPA and tcuPA as each rPAI-1 protein concentration was increased. These results indicated that both rPAI-1$_{23}$ and rPAI-1$_{A23}$ bind scuPA. As the concentration of rPAI-1 was increased, the binding interactions with uPA altered the conformation of uPA such that the epitope was not recognized by the antibody. When 30 nM of rPAI-1$_{A23}$ were reacted with scuPA, there was a substantial upward shift in the molecular mass of scuPA. Since the reacted proteins were electrophoresed on an SDS, non-reducing polyacrylamide gel, these data indicate that a covalent bond was formed between the two proteins.

The rPAI-1 proteins were also reacted with tcuPA and the reaction mix was probed for uPA. There was a slight upward shift in the molecular mass of tcuPA that had been reacted with plasminogen, 3 nM rPAI-1$_{23}$, and 3 nM rPAI-1$_{A23}$. There was a dramatic shift in tcuPA (from near 34 kDa to greater than 52 kDa) when it was reacted with 15 and 30 nM of rPAI-1$_{23}$. There was also a significant, but less consistent upward shift in the molecular mass of tcuPA reacted with 15 and 30 nM of rPAI-1$_{A23}$. The shift in the molecular mass of tcuPA indicated that both rPAI-1$_{23}$ and rPAI-1$_{A23}$ bound tcuPA and that a covalent bond was formed in the binding interactions to account for the obvious shift in mass.

Angiostatin production was examined when rPAI-1$_{A23}$ and rPAI-1$_{23}$ were added simultaneously to a reaction mixture with plasminogen and either scuPA or tcuPA. Immunoblots containing the products of the reactions were probed for angiostatin K1–3. When scuPA, rPAI-1$_{23}$, and plasminogen were added simultaneously to a reaction mixture, K1–3 were present as two distinct fragments between 34 and 50 kDa and less pronounced near 28 kDa. It appeared that the cleavage product was predominantly from plasmin. There was a slight, subtle upward shift in the molecular mass of the angiostatin fragments produced in a reaction with rPAI-1$_{23}$, tcuPA, and plasminogen. In these reactions, the angiostatin fragments were predominantly plasmin cleavage products as evidenced by the depletion in plasmin near 70 kDa. Alternatively, rPAI-1$_{23}$ may preferentially cleave plasminogen and/or bind uPA to inhibit plasmin formation altogether.

When rPAI-1$_{A23}$ was incubated with tcuPA and plasminogen, angiostatin fragments were observed near 45 kDa and between 28–34 kDa; plasmin and plasminogen were undetectable at 70–80 kDa. As the concentration of rPAI-1$_{A23}$ was increased, there was a reduction in the angiostatin fragments at 45 kDa. However, when scuPA was substituted for tcuPA, the same angiostatin fragments were present, but they were shifted upward with increasing concentrations of rPAI-1$_{A23}$. When rPAI-1$_{A23}$ was present at 30 nM, the kringle fragments were not present and plasminogen shifted to a molecular mass that exceeded the plasminogen control. Thus, uPA may have preferentially interacted with plasminogen to produce plasmin, which was then completely cleaved by rPAI-1$_{A23}$ or the complex that was formed with 30 nM of rPAI-1$_{A23}$ prevented plasmin formation and subsequent cleavage. This was evidenced biochemically by a shift in the molecular mass of plasminogen. These results demonstrate that both tcuPA and scuPA have the potential to substantially effect rPAI-1$_{A23}$-induced cleavage of plasmin into angiostatin. However, differences in the uPA conformation, that was scuPA versus tcuPA, seemingly had an effect on angiostatin processing (additional cleavage) in reactions containing rPAI-1$_{23}$. Nevertheless, in all cases, plasmin levels were depleted.

Biochemical and in vitro analysis of angiostatin formation indicated that rPAI-1$_{23}$ and rPAI-1$_{A23}$ proteins selectively modulated angiostatin formation. Accordingly, in one embodiment of the present invention, rPAI-1 proteins lacking a reactive center loop and lacking at least a portion of a heparin-binding domain may be used in a method for modulating the formation of angiostatin which contains kringles 1–3 or kringles 1–4. In a preferred embodiment, a rPAI-1 protein for use in modulating angiostatin formation is rPAI-1$_{23}$ or rPAI-1$_{A23}$.

In vitro anti-angiogenic activity of the rPAI-1 proteins was analyzed. In an Annexin V binding assay, it was demonstrated that adherent bovine aortic endothelial cells (BAEC), 39% of the rPAI-1$_{23}$ and 19% of rPAI-1$_{A23}$-treated cells, were undergoing apoptosis. Whereas, only 4–7% of the rPAI-1$_{Hep23}$, rPAI-1$_{24}$, and yeast-treated cells were apoptotic, a value comparable to the endothelial control. This indicated that heparin-binding to rPAI-1$_{Hep23}$ protects the endothelial cells from apoptosis. Therefore, proteolytic cleavage products of rPAI-1$_{23}$ and rPAI-1$_{A23}$ may be involved with the induction of apoptosis. Thus, in another embodiment of the present invention, rPAI-1 proteins lacking a reactive center loop and lacking at least a portion of a heparin-binding domain may be used in a method for stimulating apoptosis. In a preferred embodiment, a rPAI-1 protein for use in stimulating apoptosis is rPAI-1$_{23}$ or rPAI-1$_{A23}$.

To further investigate the in vitro anti-angiogenic activity of the rPAI-1 proteins, cell proliferation in the presence of rPAI-1 proteins was examined. Bovine aortic endothelial cells were evaluated for their ability to proliferate after exposure to rPAI-1 proteins. The control cells proliferated at a rate of approximately one doubling in 48 hour. The rPAI-1$_{24}$-treated cells did not double in number during the first 48 hours, but doubled in the subsequent 48 hours. The rPAI-1$_{23}$- and rPAI-1$_{A23}$-treated cells did not increase in number in the 96 hour test period. In fact, the rPAI-1$_{23}$-treated cells decreased their number by 80% between 48 and 96 hours. There were 46% fewer apoptotic rPAI-1$_{A23}$-treated cells. Nearly 100% of the rPAI-1$_{23}$- and rPAI-1$_{A23}$-treated endothelial cells examined in a BrdU labeling assay incorporated BrdU into DNA; thus supporting low density in rPAI-1$_{23}$ and rPAI-1$_{A23}$-treated cells as a result of reduced number, and not loss of proliferation capability. The heparin sulfate-binding rPAI-1 protein supports full proliferation and cell survival while the poor or non-heparin sulfate-binding proteins impair cell number. Accordingly, in another embodiment of the present invention rPAI-1 proteins lacking a reactive center loop and lacking at least a portion of a heparin-binding domain may be used in a method for effectively reducing or inhibiting cell proliferation. In a preferred embodiment, a rPAI-1 protein for use in reducing or inhibiting cell proliferation is rPAI-1$_{23}$ or rPAI-1$_{A23}$.

Experiments focusing on tubule formation were also conducted to explore the in vitro anti-angiogenic activity of the rPAI-1 proteins. Chick aortic arch rings from 14-day chick embryos formed tubules in MATRIGEL™. The tubules proliferated and migrated extensively when stimulated with bovine brain extract (BBE). The rings that were exposed to rPAI-1$_{Hep23}$-BBE had a proliferation and migration rate at least equivalent to the control. In contrast, after 3 days of exposure to rPAI-1$_{23}$-BBE, new tubules extended from the aortic rings to approximately 50% of the length measured in the control or rPAI-1$_{Hep23}$-treated rings. By day 4, that difference was 65%. The newly formed tubules from the aortic rings treated with rPAI-1$_{A23}$ migrated about 50% less than the control on day 3. That difference remained nearly the same on day 4. There was a greater amount of proliferation near the periphery of the ring of rPAI-1$_{A23}$-treated samples when compared to the rPAI-1$_{23}$-treated rings. The branches of the rPAI-1$_{23}$- and rPAI-1$_{A23}$-treated rings were more flattened and tightly connected. Their branches appeared to fuse as they extended parallel. The differences observed in the newly formed tubules in the rPAI-1-treated samples are consistent with the data presented above, where it was shown that unlike rPAI-1$_{23}$ and rPAI-1$_{A23}$, the rPAI-1$_{Hep23}$ does not induce the formation of proteolytic fragments at a 34–38 kDa molecular mass corresponding to plasminogen kringles 1–3 and does not induce apoptosis in BAEC with a concomitant reduction in cell number.

The aortic ring studies indicated that rPAI-1$_{Hep23}$ did not block migration or proliferation of sprouting tubules in MATRIGEL™. Therefore, the ability of rPAI-1$_{Hep23}$ to stimulate tubule migration and proliferation in the absence of angiogenic growth factors, bFGF and VEGF was examined in an ex vivo assay. Aortic rings stimulated with a combination of VEGF and bFGF were used as a positive control. These experiments showed that rPAI-1$_{Hep23}$ was able to stimulate angiogenic tubules at a level comparable to that observed and measured in embryonic aortic rings stimulated with combined VEGF and bFGF.

In vivo analysis of the proangiogenic properties of rPAI-1$_{Hep23}$ were also conducted. The cumulative results from three experiments indicated that proangiogenic rPAI-1$_{Hep23}$ protein stimulated 163% more neoangiogenic vessels than the MATRIGEL™ pellets containing VEGF/bFGF. The rPAI-1$_{23}$ protein, which has anti-angiogenic properties, reduced the number of neoangiogenic vessels to 1.3% of those formed in growth factor-stimulated pellets. The results indicate that rPAI-1$_{Hep23}$ has proangiogenic properties which are growth factor independent while rPAI-1$_{23}$ is anti-angiogenic.

The biochemical data provided herein demonstrated formation of a uPA·rPAI-1 complex that could possibly alter the activity of uPA or the rPAI-1 proteins. Therefore, the ability of endothelial cells to form tubes, migrate/extend, and proliferate in MATRIGEL™ following 24 hours of treatment with: each rPAI-1 protein; uPA and rPAI-1 added simultaneously, but independently; or a uPA·rPAI-1 complex were examined. Each rPAI-1 protein concentration was reduced so that uPA was in excess. It was determined that BAEC treated with rPAI-1$_{A23}$ formed a greater number of migrating tubules in MATRIGEL™ when compared to untreated or rPAI-1$_{23}$-treated BAEC. Further, connecting, migrating tubules and enhanced proliferation at focal centers were the obvious characteristics that resulted from scuPA and tcuPA treatment. The rPAI-1$_{A23}$-treated cells had fewer branch points and tubule extensions than scuPA- and tcuPA-treated cells. The rPAI-1$_{A23}$-treated endothelial cells that migrated in MATRIGEL™ formed tubules that appeared to be proliferating as they extend to result in greater tubule width; this effect was also seen in tcuPA-treated cells. Moreover, the effects of an rPAI-1$_{A23}$·tcuPA complex added to the BAEC increased proliferation at the focal centers, and increased tubule migration and extension. However, there was no apparent sprouting from the migrating tubules and the tubules appeared to be thinner. The overall effect was increased proliferation, migration and connecting of tubules, but a reduction in tubule width. Furthermore, when rPAI-$1_{A23}$ and tcuPA were added separately, but simultaneously, to the cultured cells, the tubule extension between focal centers was shortened. There was more proliferation along the migrating tubules, but the overall tubule density was reduced when compared with the tcuPA-treated cells. In addition, BAEC treated with a rPAI-$1_{A23}$·scuPA reaction mixture displayed enhanced migration of tubules that were connecting and branching, as well as increased proliferation. Those effects were reduced when rPAI-$1_{A23}$ and scuPA were added separately, but simultaneously to the cultured cells. However, rPAI-$1_{23}$ was able to maintain its inhibitory effect on tubule formation in MATRIGEL™. Following rPAI-$1_{23}$ treatment, single endothelial cells were embedded in the MATRIGEL™, but there was very little migration and proliferation of those cells. When uPA (single chain or two chain) and rPAI-$1_{23}$ were first reacted and then added to the BAEC, there was a small increase in tubule formation, extension and proliferation from the focal centers. The tubules that formed were spindly. When rPAI-$1_{23}$ and uPA were added separately but simultaneously, there was less proliferation and extension than observed in the cells that were treated with the reaction mixture. Overall, there was very little change in the anti-angiogenic effects of rPAI-$1_{23}$ when uPA was also added exogenously.

Migration of tubules appeared to be VEGF-dependent. By day 4, the rPAI-$1_{23}$-VEGF-treated rings displayed a reduction in the rate of migration similar to that measured in the BBE-treated samples. There was a significant difference in the structure of the VEGF-treated control tubules and the rPAI-$1_{23}$-VEGF-treated samples. VEGF-treated rings had a diffuse branching pattern with branches coming off at right angles, whereas the rPAI-$1_{23}$-VEGF-treated rings formed a very tightly packed mass of tubules that extended in parallel. These data show that rPAI-$1_{23}$ and rPAI-$1_{A23}$ are able to inhibit the migratory function of new sprouts from chick aortic rings stimulated with BBE. The rPAI-$1_{23}$ protein inhibits the migration of new sprouts stimulated with VEGF. In the rPAI-$1_{23}$ and rPAI-$1_{A23}$-treated aortic rings apoptosis of sprouting endothelial cells was observed. The apoptosis appeared to result in breakage of the tubule. Hence, in a further embodiment of the present invention, rPAI-1 proteins lacking a reactive center loop and lacking at least a portion of a heparin-binding domain may be used in a method for inhibiting cell migration. In a preferred embodiment, a rPAI-1 protein for use in inhibiting cell migration is rPAI-$1_{23}$ or rPAI-$1_{A23}$.

The modulation of VEGF from a complex with heparin by rPAI-1 proteins was analyzed. Variable concentrations of each rPAI-1 protein were incubated with a VEGF-heparin complex to examine the release and/or activation of VEGF-A. VEGF activation and release from the complexes were then tested in the presence of activator molecules uPA or plasmin. Western blot analysis of the complexes was conducted with an antibody against heparin-binding VEGF-A isoforms.

Experiments were conducted with the VEGF-$A_{165,189,206}$ isoform in an rPAI-1-VEGF-heparin complex containing activator molecules uPA or plasmin. When rPAI-$1_{23}$ was part of the complex, there were only traces of the 46 kDa activated VEGF-$A_{165,189,206}$. In the presence of rPAI-$1_{A23}$, VEGF was released from heparin in the absence or presence of either uPA or plasmin. Similarly, the presence of rPAI-$1_{24}$ in the mixture with VEGF-heparin resulted in the release of active VEGF at all concentrations of rPAI-$1_{24}$. In the rPAI-$1_{24}$-containing reactions, the VEGF release occurred in the presence of uPA or plasmin. Reaction mixtures containing rPAI-$1_{Hep23}$ showed activated VEGF in reactions containing low concentrations of rPAI-$1_{Hep23}$ in the absence or presence of either uPA or plasmin. At higher concentrations of rPAI-$1_{Hep23}$, there was a blockage of VEGF release and an increase in VEGF-containing fragments between 60 and 80 kDa. The high molecular mass fragments containing VEGF had cross-reactivity with VEGF-$B_{186}$ and were indicative of the 60–62 kDa active VEGF-$B_{186}$ homodimer (Cao, et al. (1999) supra). The greater than 80 kDa molecular mass containing VEGF also existed in samples containing rPAI-$1_{23}$, rPAI-$1_{A23}$, and rPAI-$1_{24}$. However, the samples containing rPAI-$1_{Hep23}$ clearly had a greater amount of VEGF-A complexed at a high molecular mass. These experiments showed that rPAI-$1_{A23}$ and rPAI-$1_{24}$ do not block the activation or release of VEGF from a complex with heparin. Although rPAI-$1_{A23}$ and rPAI-$1_{24}$ both have a partial heparin-binding domain, only rPAI-$1_{24}$ has RCL. The RCL may alter the conformation such that the partial heparin domain in rPAI-$1_{24}$ is obscured and unable to block the release of activated VEGF. On the other hand, both rPAI-$1_{23}$ and rPAI-$1_{Hep23}$ are able to block the release of VEGF from a complex with heparin. These data indicate that the heparin-binding domain in each of these two isoforms participates in blocking the release of active VEGF-A and that partial heparin-binding is more effective in blocking VEGF-A activation and/or release. These findings indicate that the ability of rPAI-$1_{23}$ to block growth and vessel sprouting may be due to its ability to block VEGF activation.

Experiments were also conducted to determine which VEGF isoforms were complexed with heparin-rPAI-$1_{23}$ at the high molecular mass as seen in the previous experiments. For these experiments, DTT was added to the final reaction mixture containing VEGF-heparin-rPAI-$1_{23}$+uPA (or plasmin) for 2.5 hour at 37° C. The rPAI-$1_{23}$-VEGF-heparin complexes contained multiple-sized VEGF fragments representative of mature or active VEGF-$A_{165,189}$: the fragment less than 34 kDa observed in this experiment corresponded to activated VEGF-$A_{189}$ (Plouet, et al. (1997) supra; Keyt, et al. (1996) *J. Biol. Chem.* 271:7788–7795); the 34–38 kDa fragments corresponded to plasmin or uPA activated VEGF-$A_{165,189}$ Plouet, et al. (1997) supra; Keyt, et al. (1996) *J. Biol. Chem.* 271:7788–7795); the 40–45 kDa fragments corresponded to uPA-matured VEGF-$A_{189}$ or VEGF-$A_{165}$ (Plouet, et al. (1997) supra; Keyt, et al. (1996) *J. Biol. Chem.* 271:7788–7795); and the 50–52 kDa band was the molecular mass of mature, but not active VEGF (Plouet, et al. (1997) supra).

In VEGF-heparin complexes containing lower concentrations of rPAI-$1_{23}$ protein, there were activated VEGF fragments between 30 and 42 kDa which corresponded to the reported sizes for processed VEGF-$A_{165,189,206}$. The fragments that migrated at 36–38 kDa were also in reactions containing uPA or plasmin. The most predominant VEGF fragment released from a VEGF-heparin-rPAI-$1_{23}$ complex was seen near 50 kDa (mature VEGF) in the absence of uPA and plasmin. When the rPAI-$1_{23}$ protein concentration was increased to 30 nM, the active VEGF at 50 kDa was absent and the products were approximately 30, 38–42 kDa which corresponded in size to uPA-matured VEGF-$A_{189}$ and VEGF-$A_{165}$, or plasmin-activated VEGF-$A_{189}$. In mixtures containing a VEGF-heparin-rPAI-$1_{Hep23}$ complex, the associated VEGF remained at a higher molecular mass (greater than 80 kDa), except when rPAI-$1_{Hep23}$ was at a low concentration. The rPAI-1$_{Hep23}$ protein conformation maintained VEGF-A$_{165,189,206}$ in a complex with heparin. Therefore, the rPAI-1$_{23}$ may be used to block the release of multiple forms of matured, activated, and processed (uPA and plasmin cleaved) VEGF-A fragments reported for heparin-binding VEGF-A$_{165,189}$ isoforms.

Analysis of VEGF-A contained within the culture medium of rPAI-1-treated endothelial cells was also conducted. The rPAI-1$_{23}$-treated cells primarily contain VEGF-A fragments at a molecular mass greater than 50 kDa. A small fraction of VEGF fragments at a molecular mass less than 50 kDa were also observed in the rPAI-1$_{23}$-treated samples. The fragments greater than 50 kDa were representative of mature or pro-VEGF and those less than 50 kDa corresponded to active VEGF. In the culture medium samples collected rPAI-1$_{A23}$-treated cells there was an abundance of VEGF-A fragments at a molecular mass of ~36–45 kDa at all time points (6, 15, 24, 30, 48, and 72 hours). This molecular mass corresponded to active or uPA/plasmin processed, active VEGF-A. All rPAI-1A$_{23}$-treated samples also contained mature or pro-VEGF at a molecular mass greater than 50 kDa. One of the inactive fragments in the 15 hour time point sample was absent in samples at 6, 24, 30, 48, and 72 hours. The culture media from all untreated and rPAI-1$_{24}$-treated cells, contained active VEGF and a small amount of processed, activate VEGF. The culture medium samples from the rPAI-1$_{Hep23}$-treated cells primarily contained inactive VEGF and lesser amounts of processed, active VEGF. The results of these experiments clearly showed that VEGF in rPAI-1$_{A23}$-treated culture medium contains a much greater amount of active VEGF, mostly representative of uPA or plasmin processed VEGF. Similar VEGF fragments were absent or present to a lesser degree in the untreated or rPAI-1$_{23}$-, rPAI-1$_{Hep23}$-, and rPAI-1$_{24}$-treated cells. The culture media from rPAI-1$_{24}$-treated and untreated cells contained a greater amount of active, unprocessed VEGF than the media from rPAI-1$_{23}$, rPAI-1$_{A23}$-, or rPAI-1$_{Hep23}$-treated cells. These data corresponded with the biochemical analysis of VEGF released from a complex with heparin and rPAI-1 proteins. The molecular mass of all of the VEGF fragments corresponded to dimeric VEGF-A despite the rigorous reducing conditions applied to all samples.

Differences in heparan sulfate-bound VEGF-A isoforms in rPAI-1-treated cells were analyzed using two different antibodies. Immunoblots were probed for VEGF-A with an antibody specific for epitopes common to VEGF-A$_{165,189,205}$. The results of these experiments showed that, at the 12-hour time point, the rPAI-1$_{Hep23}$- and rPAI-1$_{24}$-treated cells contained two fragments of VEGF-A at a molecular mass near 58 kDa. In the rPAI-1$_{23}$-treated, rPAI-1$_{A23}$-treated, and untreated samples, VEGF-A was absent or barely visible. However, when two competing antibodies specific for VEGF-A were simultaneously incubated with immunoblots containing proteins released from a heparinase digest, the rPAI-1$_{23}$-treated, rPAI-1$_{A23}$-treated, and untreated cells show VEGF-A released from heparan sulfate. Among the samples, the rPAI-1$_{23}$-treated cells at the six-hour time point had the greatest amount of detectable VEGF-A released in the enzymatic digest. The VEGF was seen as two distinct fragments with a small difference in molecular mass. Each fragment corresponded to the molecular mass of dimeric VEGF, despite the rigorous reducing conditions. By 12 hours, VEGF was not detected in rPAI-1$_{23}$-treated cells. However, at the 12-hour time point, the rPAI-1$_{A23}$-treated and the untreated cells showed a variable molecular mass in VEGF released as a result of the digest.

The VEGF fragments in the rPAI-1$_{23}$-treated samples were very close to 50 kDa, whereas, the VEGF fragments in the untreated and the rPAI-1$_{A23}$-treated cells corresponded to a molecular mass that was more representative of VEGF-A$_{189}$ or VEGF-A$_{206}$. The rPAI-1$_{Hep23}$- and rPAI-1$_{24}$-treated cells did not show the release of heparan sulfate-bound VEGF when the blot was probed with competing antibodies. The results of these sets of experiments showed that different VEGF-A isoforms were released with the heparinase digest, depending upon the rPAI-1 treatment. The use of competing antibodies exposed binding sites in rPAI-1$_{23}$-treated, rPAI-1$_{A23}$-treated, and untreated cells that were not detected with the single antibody probe for VEGF-A$_{165,189,205}$. The most pronounced difference was the intensity and molecular mass of VEGF-A at the 6-hour time point in rPAI-1$_{23}$-treated cells. It corresponded to a molecular mass near that reported for dimeric mature/pro-VEGF-A$_{165}$ and/or mature VEGF-A$_{189}$. Because the VEGF fragments became intensely visible upon competition with an antibody specific for the active site of VEGF-A$_{165}$, the data indicated that the fragments slightly above 50 kDa were VEGF-A$_{165}$. These data also showed that the conformation of VEGF was altered as a result of rPAI-1$_{23}$ treatment. Also, the presence of extracellular matrix-associated VEGF-A at the 6-hour time point was coordinate with the absence of activated VEGF in the culture medium of rPAI-1$_{23}$-treated cells at 6 hours. The VEGF-A fragments that become visible at the 12 hour time points in untreated or rPAI-1$_{A23}$-treated cells were at a greater molecular mass corresponding to pro-VEGF-A$_{189}$ or pro-VEGF-A$_{206}$, the isoforms that had the greatest affinity for heparan sulfate. Similarly, the VEGF detected in all samples was representative of dimeric VEGF, despite the reducing conditions.

In vitro experiments were conducted with Annexin V to measure apoptosis in bovine and porcine aortic endothelial cells treated with rPAI-1$_{23}$ protein. These data showed that rPAI-1$_{23}$ treatment resulted in 300% more apoptotic bovine aortic endothelial cells (BAEC) as compared to porcine aortic endothelial cells (PAEC). Since PAEC do not express VEGFR-1 or VEGFR-2, these experiments clearly showed that most, but not all, of the apoptosis induced by rPAI-1$_{23}$ was through a mechanism that blocked/inhibited VEGF receptors 1 and/or 2.60% of the apoptosis in rPAI-1$_{23}$-treated BAEC could be attributed to inhibition of VEGFR functional activity. These data demonstrate a mechanism whereby rPAI-1$_{23}$ blocked release of active VEGF-A thereby preventing (or limiting) binding to VEGF receptors to result in apoptosis. The 65% reduction in migration of VEGF-stimulated tubules from rPAI-1$_{23}$-treated embryonic chick aortic rings provides a mechanism which inhibits VEGFR-2 function. Accordingly, in a further embodiment of the present invention, rPAI-1 proteins used to block the release of VEGF from a VEGF-heparin complex lack an RCL domain and lack all or at least a heparin-binding domain as found in, for example, rPAI-1$_{23}$, rPAI-1$_{24}$ and rPAI-1$_{Hep23}$. In a preferred embodiment, rPAI-1$_{23}$ is used to block the release of VEGF from a VEGF-heparin complex.

PAI-1 can be cleaved at the P1 and P'1 residues of the RCL, resulting in a substrate with a molecular mass of 39 kDa (Dhanabal, et al. (1999) *J. Biol. Chem.* 274:11721–11726; Aleshkov, et al. (1996) *J. Biol. Chem.* 271:21231–21238; Declerck, et al. (1992) *J. Biol. Chem.* 267:11693–11696). The amount of substrate PAI-1 (RCL cleaved, inactive) is increased during the interaction with PAI-1 with thrombin in the presence of heparin and vitronectin (Van Meijer, et al. (1997) *Blood* 90:1874–1882). A smaller, cleaved PAI-1 fragment (<31 kDa) has been shown to be produced as a result of addition of heparin and thrombin to a pre-existing PAI-1/thrombin complex (Patston and Schapira (1994) *Blood* 84:1164–1172). The deletions at the carboxy-terminus exclude the RCL in three of the four rPAI-1 isoforms described herein and each of these proteins function differently with respect to pro- and anti-angiogenic mechanisms. Therefore, the functional activity of these proteins is not solely dependent upon the absence of the reactive center loop. The structural difference in rPAI-1$_{23}$, rPAI-1$_{A23}$, and rPAI-1$_{Hep23}$ is the heparin (heparan sulfate)-binding domain which accounts for the differences in functional activity of the three proteins. The novel functional activity of these isoforms of PAI-1 makes them useful in differentially modulating angiogenesis. In a preferred embodiment of the present invention, an rPAI-1 isoform lacking an RCL domain and lacking a least a portion of the heparin-binding domain is useful in a method of blocking, reducing or decreasing angiogenesis. Exemplary isoforms lacking an RCL domain and at least a portion of the heparin-binding domain include, but are not limited to, rPAI-1$_{23}$ and rPAI-1$_{A23}$. In another preferred embodiment of the present invention, an rPAI-1 isoform lacking an RCL domain and containing a complete heparin-binding domain is useful in a method of stimulating or increasing angiogenesis. An exemplary isoform lacking an RCL domain and containing a complete heparin-binding domain includes, but is not limited to, rPAI-1$_{Hep23}$.

The rPAI-1$_{23}$, rPAI-1$_{Hep23}$ and rPAI-1$_{A23}$ isoforms of the present invention are useful in treating diseases or processes that are mediated by, or involve, angiogenesis. The present invention provides a method of treating an angiogenesis-mediated disease with an effective amount of a PAI-1 isoform lacking the RCL domain and either containing a complete heparin-binding domain or lacking at least a portion of the heparin-binding domain. It is contemplated that rPAI-1 isoforms lacking the RCL domain and lacking at least a portion of the heparin-binding domain, e.g., rPAI-1$_{A23}$ and rPAI-1$_{23}$, would be useful as anti-angiogenic agents. Angiogenesis-mediated diseases for which anti-angiogenic agents would be useful in alleviating the signs or symptoms of include, but are not limited to, solid tumors; blood bourne tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Anti-angiogenic agents are also useful in the treatment of diseases that have angiogenesis as a pathologic consequence such as cat scratch disease (Rochele minalia quintosa) and ulcers (Helobacter pylori). Furthermore, PAI-1 isoforms lacking the RCL domain and lacking at least a portion of the heparin-binding domain are effective in the treatment of disease of excessive or abnormal stimulation of endothelial cells. These diseases include, but are not limited to, intestinal adhesions, atherosclerosis, scleroderma, and hypertrophic scars, i.e., keloids.

Further contemplated is rPAI-1 isoforms lacking the RCL domain and containing a complete heparin-binding domain, e.g., rPAI-1$_{Hep23}$, as proangiogenic agents. Proangiogenic agents would be useful for stimulating wound healing, replacing clogged arteries to improve circulation in patients with arterial clogging, and treating various types of heart disease to promote the growth of blood vessels thereby reducing the need for bypass surgery.

While specific PAI-1 isoforms are disclosed herein, it would be well within the ability of the skilled artisan, using the results provided by this disclosure, to generate additional PAI-1 isoforms lacking at least a portion of the heparin-binding domain. For example, one could remove residue Lys-65 and/or Lys-69 of the rPAI-1$_{Hep23}$ isoform to decrease the proangiogenic activity of this isoform.

In general, those skilled in the art will appreciate that minor deletions or substitutions may be made to the amino acid sequences of rPAI-1 isoforms of the present invention without unduly adversely affecting the activity thereof. Thus, isoforms containing such deletions or substitutions are also contemplated. In isoforms containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; KGln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

The rPAI-1 isoforms of the present invention may be purified from host cells which express the same, in accordance with known techniques, or even manufactured synthetically. Alternatively, the rPAI-1 isoforms may be used as part of a gene therapy approach.

Recombinant PAI-1 proteins may be produced using methods exemplified herein for using other well-known methods for long-term, high-yield production of recombinant proteins. For example, nucleic acid sequences encoding, e.g., human, porcine, or bovine PAI-1, may be recombinantly engineered, using well-known methods, to produce the rPAI-1 isoforms of the present invention which lack the RCL domain and contain a complete heparin-binding domain or lack at least a portion of a heparin-binding domain as defined herein. A recombinant nucleic acid sequence encoding a rPAI-1 isoform may then be incorporated into an expression vector. An expression vector is a replicable DNA construct in which a nucleic acid sequence encoding an rPAI-1 isoform of the present invention is operably linked to suitable control sequences capable of effecting the expression of the isoform in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites that are operably linked to the gene to be expressed and are operable in the host organism.

Suitable host cells include prokaryotes, yeast cells, or higher eukaryotic organism cells. Prokaryote host cells include gram negative or gram positive organisms, for example *Escherichia coli* (*E. coli*) or *Bacilli*. Higher eukaryotic cells include established cell lines of mammalian origin. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar, et al., ((1977) *Gene* 2:95). Promoters most commonly used in recombinant microbial expression vectors include the beta-lactamase (penicillinase) and lactose promoter systems (Chang, et al. (1978) *Nature* 275:615; Goeddel, et al. (1979) *Nature* 281:544), a tryptophan (trp) promoter system (Goeddel, et al. (1980) *Nucl. Acids Res.* 8:4057; EP36,776) and the tac promoter (De Boer, et al. (1983) *Proc. Natl. Acad. Sci. USA* 80:21). The promoter and Shine-Dalgarno sequence (for prokaryotic host expression) are operably linked to the DNA of the present invention, i.e., they are positioned so as to promote transcription of the messenger RNA from the DNA.

Eukaryotic microbes such as yeast cultures may be transformed with suitable expression vectors as exemplified herein. Alternatively, *Saccharomyces cerevisiae* may be used. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb, et al. (1979) *Nature* 282:39; Kingsman, et al. (1979) *Gene* 7:141; Tschemper, et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Cultures of cells derived from multicellular organisms are also desirable hosts for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment that also contains the SV40 viral origin of replication. See Fiers, et al. (1978) *Nature* 273:113. Further, the protein promoter, control and/or signal sequences may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, *Trichoplusia ni* MNPV, *Rachiplusia ou* MNPV, or *Galleria ou* MNPV) may be employed to make proteins useful in carrying out the present invention, as described in U.S. Pat. Nos. 4,745,051 and 4,879,236. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding an rPAI-1 may be ligated into an adenovirus transcription/translation complex consisting of the late promoter and tripartite leader sequence. Insertion in a non-essential E1 or E3 region of the viral genome may be used to obtain a viable virus which is capable of expressing the rPAI-1 in infected host cells (Logan and Shenk (1984) *Proc. Natl. Acad. Sci.* 81:3655–3659). In addition, transcription enhancers, such as the Rous sarcoma virus (RSV) enhancer, may be used to increase expression in mammalian host cells.

Rather than using vectors that contain viral origins of replication, one may transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival or transformants in culture medium that is toxic, or from which the cells cannot obtain critical nutrition without having taken up the marker protein.

Depending on the host cell to be transformed, any well-known means of introducing the expression vector containing nucleic acid sequences encoding an rPAI-1 may be used. Following the introduction of the expression vector, cells may be allowed to grow for 1–2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, et al. (1977) *Cell* 11:223–32) and adenine phospho-ribosyltransferase (Lowy, et al. (1980) *Cell* 22:817–23) genes which can be employed in tk- or aprt-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides neomycin and G-418 (Colbere-Garapin, et al (1981) *J. Mol. Biol.* 150:1–14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan (1988) *Proc. Natl. Acad. Sci.* 85:8047–51). Alternatively, visible such as anthocyanins, β glucuronidase and its substrate GUS, and luciferase and its substrate luciferin, may be used not only to identify transformants, but also to quantify the amount of transient or stable protein expression attributable to a specific vector system (Rhodes, et al. (1995) *Methods Mol. Biol.* 55:121–131).

Host cells transformed with nucleotide sequences encoding an rPAI-1 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode an rPAI-1 may be designed to contain signal sequences which direct secretion of the rPAI-1 through a prokaryotic or eukaryotic cell membrane. Other constructions may be used to join sequences encoding an rPAI-1 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the rPAI-1 may be used to facilitate purification. One such expression vector provides for expression of a fusion protein containing an rPAI-1 and a nucleic acid encoding six histidine residues preceding a thioredoxin or an enterokinase cleavage site. The histidine residues facilitate purification on IMAC (immobilized metal ion affinity chromatography) (see, e.g., Porath, et al. (1992) *Prot. Exp. Purif.* 3:263–281) while the enterokinase cleavage site provides a means for purifying the rPAI-1 from the fusion protein. A discussion of vectors which contain fusion proteins is provided in Kroll, et al. (1993) *DNA Cell Biol.* 12:441–453).

In addition to recombinant production of the rPAI-1 isoforms may be produced by direct peptide synthesis using solid-phase techniques (Merrifield (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Various fragments of the rPAI-1 isoforms may be chemically-synthesized separately and combined using chemical methods to produce the full-length molecule.

Recombinant proteins provided herein may be used as isolated and substantially purified proteins in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the PAI-1 proteins may be incorporated into biodegradable polymers allowing for sustained release of the proteins, the polymers being implanted in the vicinity of where drug delivery is desired, for example, at the site of a tumor or implanted so that the rPAI-1 isoform is slowly released systemically. Osmotic minipumps may also be used to provide controlled delivery of high concentrations of rPAI-1 through cannulae to the site of interest, such as directly into a metastatic growth or into the vascular supply to that tumor. The biodegradable polymers and their use are described, for example, in detail in Brem et al. ((1991) *J. Neurosurg.* 74:441–446).

It is contemplated that the rPAI-1 isoforms of the present invention may be co-administered. For example, rPAI-1$_{23}$ and rPAI-1$_{A23}$ may be used in a combination therapy for enhancing the formation of angiostatin and/or modulating angiogenesis.

The rPAI-1 formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

It is further contemplated that the rPAI-1 isoforms may be administered via stem cells which are genetically engineered to produce the rPAI-1 isoform.

Cells to be targeted by the rPAI-1 protein formulations include, but are not limited to, an endothelial cell, a lymphocyte, a macrophage, a glia cell, a fibroblast, a liver cell, a kidney cell, a muscle cell, a cell of the bone or cartilage tissue, a synovial cell, a peritoneal cell, a skin cell, an epithelial cell, a leukemia cell or a tumor cell.

The present invention provides administration of an "effective amount" of rPAI-1 proteins to modulate angiogenesis or angiogenic processes or treat angiogenesis-mediated diseases. An "effective amount" is considered an amount of protein empirically determined to be necessary to achieve a reproducible change in cell proliferation or apoptosis (as determined by microscopic or macroscopic visualization and estimation of cell doubling time, or of nucleic acid synthesis assays) or migration (as determined by microscopic or macroscopic visualization) or in reducing the signs or symptoms of an angiogenesis-mediated disease as would be understood by one of ordinary skill in the art.

The specific amount of rPAI-1 protein required by each individual will be dependent upon the age, health, and weight of the recipient, kind of concurrent treatment, if any, frequency of treatment, and the nature of the effect desired.

The rPAI-1 isoforms of the present invention may be used to promote in vitro production of blood vessels for transplantation.

The rPAI-1 isoforms of the present invention are also useful in the formation of angiostatin containing K1–3 and/or K1–4. Angiostatin formation may be in vivo for therapeutic purposes or in vitro for recombinant, large-scale production of angiostatin with desired activity. It is contemplated that rPAI-$1_{23}$ and rPAI-$1_{A23}$ may be used alone or in combination to form the desired angiostatin.

The examples, which follow, are set forth to illustrate methods of the present invention, and are not to be construed as limiting thereof.

EXAMPLE 1

PAI-1 Gene Deletions

The DNA encoding the truncated PAI-1 proteins was obtained by deleting the porcine PAI-1 gene (poPAI-1) (Bijnens, et al. (1997) *Thromb. Haemost.* 77:350–356; Accession number Y11347); SEQ ID NO:9). The selection of gene fragments was based on the poPAI-1 sequences that correspond to the human PAI-1 gene (huPAI-1) (Bosma, et al. (1988) *J. Biol. Chem.* 263:9129–9141; Accession number J03764; SEQ ID NO:10) sequence reported to code for functional domains in human PAI-1 (Reilly and Hutzelmann (1992) supra). Each DNA fragment was isolated from porcine aortic endothelial cells by reverse transcribing RNA into cDNA. The cDNA was made double-stranded in a polymerase chain reaction (PCR) containing porcine PAI-1-specific primers. Primers for rPAI-$1_{23}$ amplification are known, for example, Mulligan-Kehoe, et al. ((2001) supra). Primers used to PCR amplify the cDNA into double-stranded DNA coding for rPAI-$1_{A23}$ are 5' primer: 5'-G GAATTCATGGATGAGATCAGCACGG-3' (SEQ ID NO:3) and 3' primer: 5'-GC TCTAGATTTCCACTGGCTGATG-3' (SEQ ID NO:4). The resulting product corresponds to nucleotides 471–999 of poPAI-1 and 265–793 of huPAI-1. Likewise, primers used to PCR amplify the cDNA into double-stranded DNA coding for rPAI-$1_{Hep23}$ are 5' primer: 5'-G GAATTCATGCAGTTCAAGATTGAGGAGAAGGGC-3' (SEQ ID NO:5) and 3' primer: 5'-GC TCTAGATTTCCACTGGCTGATG-3' (SEQ ID NO:6). The resulting product corresponds to nucleotides 390–999 of poPAI-1 and 184–793 of huPAI-1. Furthermore, primers used to PCR amplify the cDNA into double-stranded DNA coding for rPAI-$1_{24}$ are 5' primer: 5'-G GAATTCAAGGAGCTCATGG-3' (SEQ ID NO:7) and 3' primer: 5'-GCTCTAGATCAAGGCTCCATCAC-3' (SEQ ID NO:8). The resulting product corresponds to nucleotides 444–1346 of poPAI-1 and 238–1162 of huPAI-1. Underlined nucleotides denote restriction enzyme recognition sequences. PCR conditions for amplification of all three genes are known to one skilled in the art, for example, Reilly and Hutzelmann ((1992) supra). The PCR-amplified rPAI-1 DNA fragments were double-digested with EcoRI and XbaI (Roche, Indianapolis, Ind.) to create overhangs. The restricted DNA was ligated into *Pichia pastoris* yeast shuttle vector pGAPZαA (INVITROGEN™, Carlsbad, Calif.). The TOP 10 strain of *Escherichia coli* was transformed by electroporation as described (Mulligan-Kehoe, et al. (2001) supra). Following an overnight incubation at 37° C., colonies were selected and grown in low salt LB broth for 5–7 hours at 37° C. The DNA from each colony was isolated using a miniprep kit (Qiagen, Inc. Valencia, Calif.) to identify a clone containing each gene insert. Positive isolates were identified by restriction enzyme digests and were verified by sequencing. Each recombinant protein was expressed in *P. pastoris* as described (Reilly and Hutzelmann (1992) supra) and purified by affinity chromatography. The sequences of rPAI-$1_{23}$, rPAI-$1_{A23}$, rPAI-$1_{Hep23}$, and rPAI-$1_{24}$ DNA matched the known sequence of the corresponding segment of porcine PAI-1 DNA. Each rPAI-1 protein corresponded to its expected molecular weight.

EXAMPLE 2

Anti-Angiogenic Effects of rPAI-1 Proteins

Characterization of the rPAI-1 Protein Interactions with heparin, uPA, and Plasminogen. The functionality of the rPAI-1 proteins was first tested by incubating each truncated protein with uPA and plasminogen to assess the proteolytic activity of the products of the reaction, as known in the art, for example Mulligan-Kehoe, et al. ((2001) supra). The functionality of each rPAI-1 isoform was then tested in a reaction with heparin bound to Sepharose beads. First, the rPAI-$1_{23}$, rPAI-$1_{A23}$, rPAI-$1_{Hep23}$, and rPAI-$1_{24}$ proteins (20 µg) were each incubated with 50 µl of heparin-bound Sepharose beads (Amersham Pharmacia Biotech, Piscataway, N.J.) for 2 hours at 37° C. The unbound protein was separated from the heparin-Sepharose-bound protein complex by microcentrifugation at 4° C. for 15 minutes. The proteins bound to the Sepharose beads were washed in TBS/Tween-20 followed by TBS washes. Bound samples were reacted with uPA (0.5 IU/1 µg or rPAI-1 protein) at 37° C. for 1 hour followed by a second one hour, 37° C. incubation with plasminogen (1 IU/1 µg of rPAI-1 protein). The reaction samples were analyzed on a 15% SDS polyacrylamide gel containing 1.3% casein (zymogram) (Clowes, et al. (1990) *Circ. Res.* 67:61–67; Allaire, et al. (1998) *Circulation* 98:249–255). The electrophoresed samples were incubated overnight at 37° C. in 50 mM Tris-HCl, pH 7.9, buffer containing 5 mM $CaCl_2$ to enable plasmin degradation of casein.

Identification of Plasminogen Kringle Domains. Protein products from the reaction of rPAI-1, uPA and plasminogen were electrophoresed on a 4–20% SDS polyacrylamide gel and transferred to nitrocellulose. The blots were probed with an antibody (1 µg/ml), specific for plasminogen kringles 1–3 (R&D Systems, Inc., Minneapolis, Minn.). Following a 1 hour, room temperature incubation with the primary antibody, a secondary rabbit anti-goat IgG HC+LC polyclonal antibody (Pierce, Rockford, Ill.) at a concentration of 1 µg/ml was incubated with the anti-kringle-probed membrane for 1 hour at room temperature. A horseradish peroxidase-conjugated antibody (donkey anti-rabbit IgG, Amersham, Arlington Heights, Ill.) diluted 1:5000 amplified the binding reaction which was ultimately detected by addition of a chemiluminescent substrate (Amersham Pharmacia).

In vitro Angiostatin Production in rPAI-1 Treated Cells. Bovine aortic endothelial cells (BAEC) were plated in six-well culture plates. When the cells reached confluence, fresh growth medium containing either rPAI-1$_{23}$ or rPAI-1$_{A23}$ (1.2 nM) was added; untreated endothelial cells served as the control. The cell culture media and the extracellular matrix with associated cells were collected from the untreated, rPAI-1$_{23}$- or rPAI-1$_{A23}$-treated BAEC in a 6, 15, 24, 36, 48, and 72 hour time course, using a standard method (Mulligan-Kehoe, et al. (2001) supra). The concentration of protein in each sample from the time course was measured in a Bradford assay (Bradford (1976) *Anal. Biochem.* 72:248–254). Equivalent amounts of protein from each sample were analyzed for proteolytic activity on casein zymograms, using well-known methods (Mulligan-Kehoe, et al. (2001) supra).

Identification of plasminogen cleavage products from rPAI-1 protein, uPA, and plasminogen reactions. Either rPAI-1$_{23}$ or rPAI-1$_{A23}$ protein (3, 15, 30 nM) was incubated with two-chain uPA (0.5, 0.25, 0.05, 0.025 IU) for one hour at 37° C. Two-chain uPA is required for cleavage of plasminogen into plasmin. After one hour, plasminogen (1 IU) was added to the uPA/rPAI-1 reaction mix, and incubated for an additional one hour at 37° C. The order in which the reactants were added was varied, but in each case the incubation time and temperature remained the same. The permutations that were used were: 1) rPAI-1 protein and tcuPA, then plasminogen; 2) tcuPA and plasminogen, then rPAI-1 protein; 3) rPAI-1 protein, tcuPA, and plasminogen reacted simultaneously.

Reaction mixtures containing rPAI-1 protein, uPA and plasminogen were electrophoresed and transferred to nitrocellulose. The reaction mixtures were then used for immunoblot analysis. Immunoblots were probed with antibodies specific for different plasminogen epitopes. All primary antibodies were used at a concentration of 1 µg/ml. The plasminogen-specific antibodies were raised against either K1–3 (R&D Systems, Inc., Minneapolis, Minn.), K4 (American Diagnostica, Greenwich, Conn.), or mini-plasminogen (American Diagnostica). Mini-plasminogen is defined by the vendor as K5 plus the serine protease domain. The antibody to mini-plasminogen does not recognize complexed plasmin. The membranes were probed for K1–3. The membranes probed for K4 or mini-plasminogen were first incubated with 1 µg/ml of the epitope-specific primary antibodies for one hour at room temperature. Then a rabbit anti-mouse IgG HC+LC (Pierce, Rockford, Ill.) polyclonal antibody at a concentration of 1 µg/ml was incubated with each membrane for 1 hour at room temperature. A horseradish peroxidase-conjugated antibody (donkey anti-rabbit IgG, Amersham, Arlington Heights, Ill.) amplified the binding reaction which was ultimately detected by addition of a chemiluminescent substrate (Amersham Pharmacia).

Plasminogen cleavage products in reactions containing rPAI-1 and plasminogen. The rPAI-1$_{23}$ and rPAI-1$_{A23}$ proteins (3, 15, and 30 nM) were each incubated with plasminogen (1 Unit) for two hours at 37° C. The proteins were denatured at 100° C. for five minutes before electrophoresis on a 10–20% SDS, non-reducing, polyacrylamide gel. The proteins were transferred to a nitrocellulose membrane and probed for mini-plasminogen.

Binding interactions of rPAI-1 and uPA. Each rPAI-1 protein (3, 15, and 30 nM) was incubated with 0.5 IU of either scuPA or tcuPA for two hours at 37° C. The reaction mixture was electrophoresed on a 4–20%, SDS, non-reducing polyacrylamide gel. The proteins were transferred to nitrocellulose. The immunoblots were incubated for one hour at room temperature with 1 µg/ml of a monoclonal antibody raised against an epitope in the B-chain of uPA near the catalytic domain (American Diagnostica). This antibody recognizes single-chain and two-chain uPA. A secondary rabbit anti-mouse IgG HC+LC (Pierce, Rockford, Ill.) polyclonal antibody at a concentration of 1 µg/ml was incubated with the membrane for one hour at room temperature. A horseradish peroxidase-conjugated antibody (donkey anti-rabbit IgG, Amersham, Arlington Heights, Ill.) amplified the binding reaction which was ultimately detected by addition of a chemiluminescent substrate (Amersham Pharmacia).

Apoptosis Detection. Bovine aortic endothelial cells (BAEC) were plated at a density of $1.0 \times 10^6$ cells/T-75 culture flask containing Dulbecco's Modified Eagle's Medium (DMEM) (Gibco BRL, Gaithersburg, Md.) supplemented with 10% fetal bovine serum, penicillin/streptomycin (100 IU/ml), and L-glutamine (0.292 mg/ml) (Gibco BRL, Gaithersburg, Md.). The cells were incubated for 24 hours at 37° C., 5% $CO_2$ before adding 3 nM of either exogenous rPAI-1$_{23}$, rPAI-1$_{A23}$, rPAI-1$_{Hep23}$, rPAI-1$_{24}$ or supernatant from *P. pastoris* culture medium. The cells were incubated an additional 48 hour at 37° C. Adherent cells were trypsinized, resuspended in DMEM containing 10% FBS, and incubated at 37° C. for 10 minutes, then pelleted. The pelleted cells were washed twice with cold Hanks' balanced salt solution (HBSS). Fluorescein isothiocyanate (FITC) conjugated APOPNEXIN™ and propidium iodide (PI) were added to the cells following the manufacturer's protocol (Integren, Purchase, N.Y.) (Koopman, et al. (1994) *Proc. Natl. Acad. Sci. USA* 84:1415–1420). Each cell fraction was analyzed separately on a FACScan (Becton Dickenson, San Jose, Calif.). The data represent five separate experiments, each performed in duplicate.

Proliferation. Bovine endothelial cells, treated with exogenous rPAI-1 protein, were plated into 6-well culture plates at a density of $1.0 \times 10^4$/ml to assess their proliferative properties in the presence of rPAI-1 proteins. The cells were trypsinized and counted on a hemocytometer plate at 48 and 96 hours after adding exogenous rPAI-1. To further ascertain the proliferative properties of the rPAI-1-treated cells, a BrdU labeling assay was performed using a FITC-labeled BrdU-specific antibody. The addition of PI enabled a microscopic count of the proliferating cells relative to the total number of cells. BrdU was added to the culture medium to obtain a final concentration of 10 µM. Cells were incubated for 30 minutes at 37° C. in a $CO_2$ incubator and then washed twice in phosphate buffered saline (PBS) containing 1% bovine serum albumin (BSA). FITC-conjugated anti-BrdU was diluted 2.5-fold in 0.5% Tween 20/PBS and added directly to the cell culture medium for 30 minutes at room temperature. The cells were washed in PBS and incubated with PI for 1 minute. Incorporation of BrdU was calculated by counting the number of cells containing FITC stain (green) or PI stain (red) in 5 fields/sample in triplicate experiments.

RPAI-1 Effect on Tubule Formation in a Chick Aortic Arch Ring Assay. Aortic arches were removed from fertilized chicken eggs (Oliver Merrill & Sons, Londonderry, N.H.) at day 14 of embryonic development. The eggs were cracked into a sterile 100 mm culture dish. The embryo was removed from its surroundings by cutting away the associated membranes and yolk sac. The chick embryo was placed ventral side up to surgically expose the heart and aortic arches. The heart and aortic arch were removed and placed into a sterile culture dish containing PBS to which 1% penicillin/streptomycin (Gibco BRL, Gaithersburg, Md.) was added. Arches, from which the surrounding adventitia had been removed, were cut into 0.8 mm sections. Each arch was placed into 1–5 µl of MATRIGEL™ (Kleinman, et al. (1982) *Biochemistry* 21:6188–6193) that was deposited on the bottom of a 6-well culture plate just prior to adding the ring. An additional 10 µl of ice-cold MATRIGEL™ was spread in a circle surrounding each aortic arch. The MATRIGEL™ was allowed to solidify before adding 2 ml of human endothelial-SFM basal growth medium (Gibco BRL). An rPAI-1 protein and bovine brain extract (BBE)(Clonetics, San Diego, Calif.), at 30 nM and 10%, respectively were added to each well and incubated at 37° C., 5% $CO_2$. In order to assess the characteristics of the new sprouts that could be ascribed to VEGF and the characteristics that were inhibited by rPAI-$1_{23}$, VEGF-A (100 ng/ml) and rPAI-$1_{23}$ (30 nM) were added to the culture medium containing the aortic rings. At 48 hour, additional medium containing BBE or VEGF and rPAI-1 protein was added to the aortic rings. Growth at 37° C. was continued for an additional 48 hours. Quantitative evaluation of tubule formation was performed by a blinded observer on a scale of 1–5 (least to maximum sprouting).

In experiments with rPAI-$1_{23}$ and rPAI-$1_{A23}$, when cells reached confluence, they were placed in separate wells and treated with; rPAI-$1_{23}$ or rPAI-$1_{A23}$ (0.6 nM), rPAI-$1_{23}$ or rPAI-$1_{A23}$ (0.6 nM) and 0.25 units of either scuPA or tcuPA; or a reaction containing rPAI-$1_{23}$ or rPAI-$1_{A23}$ (0.6 nM) incubated with 0.25 units of either scuPA or tcuPA for one hour at 37° C. Following 24 hours of treatment, the culture medium was removed, the cells were washed in HBSS, and isolated in 1 ml of cell dissociation buffer (Sigma, St. Louis, Mo.). The viable cells in each sample were counted and $1 \times 10^5$ cells from each sample were added to triplicate six-well plates coated with MATRIGEL™. The cells were incubated for an additional 24 hours at 37° C. Each well was photographed with a 35 mm camera at 40× and 200× magnification under a Nikon inverted microscope.

EXAMPLE 3

VEGF-A Interactions

Biochemical Interactions of a VEGF-Heparin Complex with rPAI Proteins, uPA, and Plasmin. VEGF was isolated from bovine aortic endothelial cells by first incubating the cells overnight in serum-free DMEM. The medium was changed before adding 100 µg/ml heparin (Sigma, St. Louis, Mo.) for 4 hours at 37° C. The serum-free DMEM containing the VEGF-heparin complex was precipitated in 80% ethanol. The serum-free medium from which the VEGF-heparin complex was isolated, was probed for VEGF-$A_{121}$ (Santa Cruz Biotechnology, Inc., Santa Cruz, Calif.) to insure that his non-heparin-binding VEGF isoform did not precipitate with the VEGF-heparin complex. VEGF-$A_{121}$ was not detected. The heparin-VEGF complex was incubated with rPAI-$1_{23}$, rPAI-$1_{A23}$, rPAI-$1_{Hep23}$, or rPAI-$1_{24}$ protein (3, 15, and 30 nM) for 2 hours at 37° C. Either uPA (0.25 IU) or plasmin (made from 1.0 IU plasminogen and 0.25 IU uPA) was added to the VEGF-heparin-rPAI-1 reaction. After an additional 2 hours incubation at 37° C. with uPA or plasmin, DTT, at a final concentration of 0.1 M, was added to one half of the reaction mixture for 3.5 hours at 37° C. An equal volume of each reaction mixture was denatured at 95° C., then electrophoresed on a 4–20% SDS polyacrylamide gel. The VGEF in each sample was visualized on a nitrocellulose membrane probed with monoclonal antibody to human VEGF-$A_{165,189,206}$ (BD PharMingen, San Diego, Calif.). A secondary rabbit anti-mouse IgG HC+LC polyclonal antibody (Pierce, Rockford, Ill.) was diluted to 1 µg/ml in TBS, pH 8.0, containing 5% skim milk, and incubated with anti-VEGF probed membranes for 1 hour at room temperature. A horseradish peroxidase-conjugated antibody (donkey anti-rabbit IgG, Amersham, Arlington Heights, Ill.) diluted 1:500 amplified the binding reaction which was ultimately detected by addition of a chemiluminescent substrate (Amersham, Arlington Heights, Ill.).

VEGF-A in the Culture Medium of rPAI-1-Treated Endothelial Cells. Bovine aortic endothelial cells were seeded into six-well culture plates and grown to confluence in DMEM. The confluent (quiescent) cells were treated with a single dose of rPAI-1 protein at a final concentration of 1.2 nM. At 6, 12, 15, 24, 30, 48, and 72 hours after the onset of treatment, the culture medium was removed from cells treated with each rPAI-1 protein. Equivalent amounts of protein were incubated with 0.1 M DTT for 2.5 hours at 37° C. The protein samples were electrophoresed on a 4–20% gradient, SDS-polyacrylamide gel. The proteins were transferred to a nitrocellulose membrane and probed for VEGF-$A_{165,189,206}$.

VEGF-A Bound to Heparan Sulfate in rPAI-1-treated Endothelial Cells. Bovine aortic endothelial cells were seeded into six-well culture plates and treated with rPAI-1 proteins. Following a 6- and 12-hour incubation with the rPAI-1 proteins, the culture medium was removed, the cell layer was washed twice in HBSS. The cells were incubated for 1 hour at 37° C. in 1 ml of HBSS-containing 0.05 IU of heparinase III (Sigma, St. Louis, Mo.). Following the incubation, the HBSS-containing proteins released during the enzymatic digest were collected. The proteins were concentrated in 80% ethanol. An equivalent amount of protein from each sample was incubated with 0.1 M DTT at 37° C. for 2.5 hours prior to electrophoresis in a 4–20% gradient SDS-polyacrylamide gel. The separated proteins were transferred to an immunoblot and probed for VEGF-A using an antibody specific for epitopes common to VEGF-$A_{165,189,209}$ (BD Pharmingen, San Diego, Calif.). In another series of experiments the immunoblots were probed simultaneously with two competing antibodies to VEGF-A; one antibody was specific for the active site of VEGF-$A_{165}$ (R&D Systems, Inc., Minneapolis, Minn.) and the second antibody was raised against an epitope common to VEGF-$A_{165,189,206}$. The binding reactions occurred at 4° C. for 15 hours. The binding reaction was further amplified, as described herein. The chemiluminescent detection was performed, as described herein.

EXAMPLE 4

Apoptosis in rPAI-$1_{23}$-Treated BAEC vs PAEC

Bovine aortic endothelial cells (BAEC) and porcine aortic endothelial cells (PAEC) were selected for comparison of apoptosis based on the expression of VEGFR-1 and VEGFR-2. BAEC express both receptors and PAEC does not express either receptor (Gille, et al. (2001) *J. Biol. Chem.* 276:3222–3230). BAEC and PAEC were seeded into T-25 flasks containing DMEM supplemented with 10% fetal bovine serum, penicillin/streptomycin (100 IU/ml), and L-glutamine (0.292 mg/ml). The cells were incubated at 37° C., 5% $CO_2$ until the cells reached confluence, at which time fresh culture medium containing 2.4 mM rPAI-$1_{23}$ was added to the cells. The treated cells continued to grow for an additional 36 hours before harvesting for analysis of apoptosis in an Annexin V assay.

EXAMPLE 5

Growth Factor-Independent Activity of rPAI-1$_{Hep23}$

Ex vivo Assay. The aortic arch was surgically removed from 14-day-old chick embryos, and sectioned into rings of approximately 0.8 mm. The rings were placed on MATRIGEL™ to promote tubule formation in endothelial-SFM basal growth medium containing 10% fetal bovine serum and either bFGF/VEGF (each at 50 ng/ml) or rPAI-1$_{Hep23}$ (15 nM). Growth of tubules was at 37° C., 5% $CO_2$ for 4 days. At day 2, additional medium containing growth factors or rPAI-1$_{Hep23}$ was added.

In vivo Assay. The rPAI-1$_{23}$ protein, at a concentration of 20 µg/ml, was added to 0.5 ml of MATRIGEL™ containing 25 ng/ml of VEGF and bFGF. The rPAI-1$_{Hep23}$ protein (20 µg/ml) was added to the MATRIGEL™ in the absence of bFGF/VEGF. The mixtures were kept on ice. Each test sample was injected into the right flank of eight C3H female mice. Neoangiogenic vessels were allowed to form around and into the MATRIGEL™ plug for two weeks. At the end of the test period, the MATRIGEL™ pellets were surgically removed from the animals and fixed in 2.5% paraformaldehyde. The fixed pellets were embedded in paraffin from which sections were cut. Neoangiogenic vessels were counted in five sections prepared from each pellet.

---

What is claimed is:

1. A method of stimulating angiogenesis comprising administering an effective amount of a plasminogen activator inhibitor type 1 isoform lacking a reactive center loop and containing a complete heparin-binding domain so that angiogenesis is stimulated, wherein said plasminogen activator inhibitor type 1 isoform is encoded by nucleotides 390–999 of SEQ ID NO:9 or n